United States Patent
Forsell

(10) Patent No.: US 11,883,297 B2
(45) Date of Patent: Jan. 30, 2024

(54) HIP JOINT METHOD

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 0 days.

(21) Appl. No.: 16/915,019

(22) Filed: Jun. 29, 2020

(65) Prior Publication Data
US 2021/0275310 A1    Sep. 9, 2021

Related U.S. Application Data

(63) Continuation of application No. 13/383,124, filed on Jan. 9, 2012, now abandoned.

(30) Foreign Application Priority Data

| Jul. 10, 2009 | (SE) | 0900957-2 |
| Jul. 10, 2009 | (SE) | 0900958-0 |
| Jul. 10, 2009 | (SE) | 0900959-8 |
| Jul. 10, 2009 | (SE) | 0900960-6 |
| Jul. 10, 2009 | (SE) | 0900962-2 |
| Jul. 10, 2009 | (SE) | 0900963-0 |

(Continued)

(51) Int. Cl.
*A61F 2/36* (2006.01)
*A61F 2/30* (2006.01)
(Continued)

(52) U.S. Cl.
CPC .............. *A61F 2/3603* (2013.01); *A61F 2/28* (2013.01); *A61F 2/30734* (2013.01); *A61F 2/34* (2013.01);
(Continued)

(58) Field of Classification Search
CPC .. A61F 2/34; A61F 2/4609; A61F 2002/2839; A61F 2002/347;
(Continued)

(56) References Cited

U.S. PATENT DOCUMENTS 6,991,656 B2 * 1/2006 Mears ........................ B25B 7/02
623/22.4
2002/0095214 A1 * 7/2002 Hyde, Jr. .............. A61F 2/4612
623/908

(Continued)

FOREIGN PATENT DOCUMENTS

WO    WO-9640021 A1 * 12/1996 ............. A61B 90/06

*Primary Examiner* — Christie Bahena

(57) ABSTRACT

The invention relates to a method for treating hip joint osteoarthritis with a medical device having a prosthetic part adapted to function as an articulating surface comprising a center axis generally coinciding with the acetabulum and the caput femur center axis when implanted. The method further comprises placing the prosthetic part in a through-going hole in the pelvic bone from the side opposite a concave portion of the acetabulum of the human patient, displacing at least one displaceable protruding supporting member connected to said prosthetic part such that the at least one displaceable protruding supporting member is configured to transfer load from the prosthetic part via the displaceable connection to the pelvic bone when being displaced relative said prosthetic part in a direction more perpendicular than parallel to the prosthetic part's center axis and being implanted.

20 Claims, 21 Drawing Sheets

(30) Foreign Application Priority Data

| Jul. 10, 2009 | (SE) | 0900965-5 |
| Jul. 10, 2009 | (SE) | 0900966-3 |
| Jul. 10, 2009 | (SE) | 0900968-9 |
| Jul. 10, 2009 | (SE) | 0900969-7 |
| Jul. 10, 2009 | (SE) | 0900970-5 |
| Jul. 10, 2009 | (SE) | 0900972-1 |
| Jul. 10, 2009 | (SE) | 0900973-9 |
| Jul. 10, 2009 | (SE) | 0900974-7 |
| Jul. 10, 2009 | (SE) | 0900976-2 |
| Jul. 10, 2009 | (SE) | 0900978-8 |
| Jul. 10, 2009 | (SE) | 0900981-2 |

(51) Int. Cl.
*A61F 2/34* (2006.01)
*A61F 2/28* (2006.01)
*A61F 2/46* (2006.01)

(52) U.S. Cl.
CPC ............... *A61F 2002/305* (2013.01); *A61F 2002/30205* (2013.01); *A61F 2002/30383* (2013.01); *A61F 2002/30471* (2013.01); *A61F 2002/30495* (2013.01); *A61F 2002/30576* (2013.01); *A61F 2002/30579* (2013.01); *A61F 2002/30594* (2013.01); *A61F 2002/30604* (2013.01); *A61F 2002/30736* (2013.01); *A61F 2002/30757* (2013.01); *A61F 2002/4635* (2013.01)

(58) Field of Classification Search
CPC ...... A61F 2002/3498; A61F 2002/3409; A61F 2002/3411; A61F 2002/3414; A61F 2002/3416; A61F 2002/3417; A61F 2002/3419; A61F 2002/342; A61F 2002/3422; A61F 2002/3438; A61F 2002/3445; A61F 2002/3448; A61F 2002/345; A61F 2002/3451; A61F 2002/3459; A61F 2002/3472; A61F 2002/3474; A61F 2002/3479; A61F 2002/3477; A61F 2002/348; A61F 2002/3482; A61F 2002/3485; A61B 17/56
See application file for complete search history.

(56) References Cited

U.S. PATENT DOCUMENTS

2003/0060889 A1* 3/2003 Tarabishy .......... A61B 17/1617
                                                              623/22.17
2004/0167629 A1* 8/2004 Geremakis ............ A61F 2/4014
                                                              623/23.42

* cited by examiner

HIP JOINT METHOD

This application is a continuation of U.S. application Ser. No. 13/383,124, filed Jan. 9, 2012, which is the National Stage Entry of PCT/SE2010/050817, which claims the benefit of Provisional Application Nos. 61/229,739, 61/229,743, 61/229,745, 61/229,746, 61/229,747, 61/229,748, 61/229,751, 61/229,752, 61/229,755, 61/229,761, 61/229,767, 61/229,778, 61/229,786, 61/229,789, 61/229,796, 61/229,735, 61/229,738, all filed Jul. 30, 2009, and Priority from Swedish Application Nos. 0900958-0, 0900978-8, 0900976-2, 0900974-7, 0900973-9, 0900972-1, 0900970-5, 0900969-7, 0900968-9, 0900966-3, 0900965-5, 0900963-0, 0900962-2, 0900960-6, 0900959-8, 0900957-2, 0900981-2, all filed Jul. 10, 2009, the entire contents of each application is hereby incorporated by reference in this application.

FIELD OF INVENTION

The present invention relates generally to a medical device for use in a surgical or laparoscopic method of treating hip joint osteoarthritis in a human patient.

BACKGROUND

Hip Osteoarthritis is a syndrome in which low-grade inflammation results in pain in the hip joints, caused by abnormal wearing of the Cartilage that acts as a cushion inside if the hip joint. This abnormal wearing of the cartilage also results in a decrease of the joints lubricating fluid called Synovial fluid. Hip Osteoarthritis is estimated to affect 80% of all people above 65 years of age, in more or less serious forms.

The present treatments for hip osteoarthritis comprises NSAID drugs, local injections of Hyaluronic acid or Glucocorticoid to help lubricating the hip joint, and replacing parts of the hip joint with a prosthesis through hip joint surgery.

Replacing parts of the hip joint is one of the most common surgeries to date performed at hundreds of thousand of patients in the world annually. The most common method comprises placing a metal prosthesis in Femur and a plastic bowl in Acetabulum. This operation is usually done through a lateral incision in the hip and upper thigh and through Fascia Lata and the lateral muscles of the thigh. To get access to the joint, the supporting Fibrous Capsule attached to Femur and Ilium needs to be penetrated, making it difficult to get a fully functional joint after the surgery. Femur is then cut at the neck with a bone saw and the prosthesis is placed in femur either with bone cement or without. Acetabulum is slightly enlarged using an Acetabular reamer, and the plastic bowl is positioned using screws or bone cement.

The surgery typically requires one week of hospitalization due to the increased risk of infection. The recovery process is on average about 6 weeks, but even after that the patient should not perform any physical activates that places large strain on the joint.

SUMMARY

A medical device for treating hip joint osteoarthritis in a human patient by providing at least one artificial hip joint surface is provided. The hip joint comprises an acetabulum, being a part of the pelvic bone, and a caput femur being a part of the femoral bone, and having a partly spherical form having a largest diameter. The medical device is adapted to be inserted through a hole in the pelvic bone from the opposite side from said acetabulum and to be in contact with the pelvic bone. Furthermore the medical device is adapted to transfer a load from the medical device to the pelvic bone through the contact with the pelvic bone. The use of this medical device enables an operational method that could spare the Fibrous Capsule and reduce the removal of healthy Femur bone. This could also shorten the time for recovery of the patient, and reducing the amount of affected large blood vessels, thus reducing the risk of blood clots.

According to one embodiment the medical device has a largest diameter which is adapted to be changed during an operation for treating hip joint osteoarthritis in a human patient by providing at least one artificial hip joint surface. According to one embodiment the medical device is adapted to have a construction, allowing the change in the largest diameter. The construction could comprises at least one slit, at least one elastic member or elastic part or at least two parts adapted to be connected to each other after insertion in a hip joint to form a functional artificial hip joint surface.

According to one embodiment, the at least one artificial hip joint surface comprises an artificial caput femur surface having a largest diameter. According to another embodiment said at least one artificial hip joint surface comprises an artificial acetabulum surface having a largest diameter. According to yet another embodiment the at least one artificial hip joint surface comprises both an artificial caput femur surface and an artificial acetabulum surface.

According to one embodiment the artificial caput femur surface is adapted to have a varying maximum diameter for insertion through a hole in the pelvic bone from the opposite side from acetabulum. The hole has a diameter smaller than the largest diameter of the caput femur.

According to one embodiment of the medical device, the artificial caput femur surface is adapted to have a varying maximum diameter for insertion through a hole in the pelvic bone from the opposite side from acetabulum. The can have a diameter smaller than the largest diameter of the artificial caput femur surface, when the artificial caput femur surface is placed in a functional hip joint.

According to another embodiment the hole has a diameter which is larger than the largest diameter of the caput femur. The hole thus being adapted to allow the caput femur to pass through said hole.

According to one embodiment the medical device is adapted to have a varying maximum diameter for insertion through a hole in the pelvic bone from the opposite side from acetabulum. The hole has a diameter smaller than the largest diameter of the artificial acetabulum surface, when said artificial acetabulum surface is placed in a functional hip joint.

According to yet another embodiment of the medical device the hole has a diameter and the largest diameter of the artificial acetabulum surface is larger than the hole, thus said medical device being adapted to hinder said artificial acetabulum surface from passing through said hole, after being placed in a functional hip joint.

According to yet another embodiment of the medical device the hole has a diameter and the largest diameter of the artificial caput femur surface is smaller than the hole, thus said medical device being adapted to allow said artificial caput femur surface to pass through said hole.

The medical device according one embodiment comprises an artificial caput femur surface comprising at least two caput femur surface parts. The at least two artificial caput femur surface parts are adapted to be connected to each other after insertion in a hip joint.

According to another embodiment the artificial acetabulum surface comprises at least two acetabulum surface parts. The at least two artificial acetabulum surface parts are adapted to be connected to each other after insertion in a hip joint of a human patient to form said artificial acetabulum surface.

According to yet another embodiment the artificial caput femur surface comprises at least two caput femur surface parts. Said at least two artificial caput femur surface parts are adapted to be connected to each other to form an assembled artificial caput femur surface having a greatest internal cross-sectional area. The assembled artificial caput femur surface is hollow and has an opening with a cross-sectional area smaller than said greatest internal cross-sectional area of said assembled artificial caput femur.

According to one embodiment said artificial caput femur surface comprises a replacement of the entire said caput femur, and according to one embodiment the artificial caput femur is smaller than said caput femur and adapted to be placed inside a surgically modified caput femur.

According to one embodiment the medical device comprises at least an artificial caput femur surface comprising a hollow ball shape replacement of the surface of said caput femur.

The contact in any of the embodiments above could be a direct or indirect contact. In the embodiments where the contact is an indirect contact a material could be placed between said medical device and said femoral bone, and/or between the medical device and the pelvic bone. Said material could be a material selected from a group consisting of: bone cement, an at least partly elastic material, glue, adhesive, antibiotic, biocompatible plastic material, biocompatible ceramics, and biocompatible metal.

The artificial acetabulum surface according to any of the embodiments above could comprise at least one supporting member. According to one embodiment the supporting member is adapted to be in connection with the pelvic bone after insertion through said hole in the pelvic bone, and further adapted to carry the load placed on caput femur from the weight of said human patient by the connection with the pelvic bone, after insertion through said hole in the pelvic bone. The supporting member could comprise at least one element selected from a group consisting of: screws, adhesive, at least one plate, bone cement, or a section of said artificial acetabulum. The at least one supporting member could be positioned on the abdominal side of said pelvic bone or on the acetabulum side of said pelvic bone, for directly or indirectly carrying said load.

According to one embodiment the said at least one supporting member is in connection with the bone surrounding the hole, said bone directly or indirectly carrying said load.

According to another embodiment the at least one supporting member is adapted to be fixated to the cortex and/or to the surface of said pelvic bone for carrying said load.

According to one embodiment the medical device comprises a first and second part, wherein said second part comprises said supporting member. The second part could be: displaceable in relation to the said first part, adapted to carry said load by the connection with the pelvic bone, and carry said load when displaced.

The caput femur has a smallest passable area, being an area of a hole through which said caput femur can pass, and the medical device has a smallest passable area, being an area of a hole through which said medical device can pass. According to one embodiment the medical device is solid, and said smallest passable area of said medical device is smaller than said smallest passable area of said caput femur.

The medical device could comprise an artificial caput femur surface and/or artificial acetabulum surface which can be adapted to be in contact with said artificial caput femur surface.

According to one embodiment the artificial acetabulum surface comprises at least one supporting member. Said at least one supporting member could be adapted to be in connection with the pelvic bone after said medical device has been inserted through said hole in the pelvic bone, and said at least one supporting member is further adapted to carry the load placed on caput femur from the weight of said human patient by the connection with the pelvic bone, after insertion through said hole in the pelvic bone.

The supporting member could comprise at least one element selected from a group consisting of: screws, adhesive, at least one plate, bone cement, or a section of said artificial acetabulum.

Said at least one supporting member could be positioned on the abdominal side and/or on the acetabulum side of said pelvic bone for directly or indirectly carrying said load.

According to one embodiment said at least one supporting member is in connection with the bone surrounding said hole, said bone directly or indirectly carrying said load. The supporting member could be adapted to be fixated to the cortex of the pelvic bone or the surface of the pelvic bone for carrying said load.

According to another embodiment said medical device comprises a first and second part, and said second part comprises said supporting member.

Method

A method of treating hip joint osteoarthritis in a human patient by providing at least one artificial hip joint surface is further provided. The hip joint comprises an acetabulum, being a part of the pelvic bone, and a caput femur being a part of the femoral bone, and having a partly spherical form having a largest diameter. The method comprises the steps of: inserting said at least one artificial hip joint surface through a hole in the pelvic bone, from the opposite side from the acetabulum, placing said artificial hip joint surface in contact with the pelvic bone direct or indirect and in connection with the caput femur or an artificial replacement therefor, and fixating said at least one artificial hip joint surface such that said artificial hip joint surface can transfer a load from said at least one artificial hip joint surface to the pelvic bone through said direct or indirect contact with the pelvic bone.

Yet another method of treating hip joint osteoarthritis in a human patient by providing at least one artificial hip joint surface is provided. The hip joint comprising an acetabulum, being a part of the pelvic bone, and a caput femur, being a part of the femoral bone. The method comprises the steps of: inserting said at least one artificial hip joint surface through a hole in the pelvic bone, from the opposite side from the acetabulum, placing said artificial hip joint surface to replace a hip joint surface of at least one of the caput femur hip joint surface and the acetabulum hip joint surface.

According to one embodiment the step of inserting said at least one artificial hip joint surface through a hole in the pelvic bone, from the opposite side from the acetabulum comprising the step of; laparoscopically operating to provide the at least one artificial hip joint surface. as to through the abdominal cavity and providing the at least one artificial hip joint surface.

According to one embodiment the step of inserting at least one artificial hip joint surface through a hole in the pelvic bone, from the opposite side from the acetabulum comprising the step of; extra abdominally operating and dissecting as to externally from the abdominal cavity providing the at least one artificial hip joint surface.

According to one embodiment the artificial hip joint surface has a largest diameter, and wherein the method further comprises the step of changing the largest diameter during an operation for treating hip joint osteoarthritis in a human patient.

According to another embodiment the artificial hip joint surface comprises at least two parts, and the method comprises the step of connecting the at least two parts to each other after insertion in a hip joint of a human patient.

The step of providing at least one hip joint surface could comprise the step of providing at least one artificial acetabulum surface.

The step of providing at least one hip joint surface could comprise the step of providing at least one artificial caput femur surface.

The at least one artificial acetabulum surface comprises at least two artificial acetabulum surface parts. The step of providing at least one artificial acetabulum surface could comprise the step of connecting said at least two artificial acetabulum parts to each other after insertion in a hip joint of a human patient to form the artificial acetabulum surface.

The at least one artificial caput femur surface could comprise at least two artificial caput femur surface parts. The step of providing at least one artificial caput femur surface could comprise the step of connecting the at least two artificial caput femur surface parts to each other after insertion in a hip joint of a human patient to form the artificial caput femur surface.

The step of providing at least one artificial caput femur surface could comprise the step of providing a replacement for the entire caput femur.

The step of providing at least one artificial caput femur surface could comprise the step of providing an artificial caput femur surface being smaller than the caput femur, and placing the artificial caput femur inside a surgically modified caput femur.

According to one embodiment the step of placing the artificial hip joint surface in contact with the pelvic bone comprises the step of placing the artificial hip joint surface in direct contact with the pelvic bone.

According to one embodiment the step of placing the artificial hip joint surface in contact with the pelvic bone could comprise the step of placing the artificial hip joint surface in indirect contact with the pelvic bone.

The method could according to one embodiment comprise the step of placing a material between said artificial hip joint surface and the pelvic bone.

The artificial acetabulum surface could comprise at least one supporting member, and the method could further comprise the steps of: placing at least one supporting member in connection with the pelvic bone, after insertion through the hole in the pelvic bone, and fixating the at least one supporting member such that the at least one supporting member can carry a load placed on caput femur from the weight of said human patient by the connection with the pelvic bone, after insertion through the hole in the pelvic bone.

The step of placing at least one supporting member could comprise the step of placing an element selected from a group consisting of: screws, adhesive, at least one plate, bone cement, and a section of said artificial acetabulum.

The method could according to one embodiment comprise the step of placing at least one supporting member in connection with the pelvic bone, which could comprise the step of placing the at least one supporting member on the abdominal side of the pelvic bone for directly or indirectly carrying a load. The step of placing at least one supporting member in connection with the pelvic bone could comprises the step of placing at least one supporting member on the acetabulum side of the pelvic bone for directly or indirectly carrying the load.

The step of placing at least one supporting member could further comprise placing at least one supporting member comprising a first and second part, wherein the second part comprises the supporting member.

According to one embodiment the method could further comprise the steps of: displacing the second part in relation to the first part, such that the second part carries the load when displaced.

Please note that any method or part of method may be combined with any other method or part of method to create any combination of methods or parts of methods.

BRIEF DESCRIPTION OF DRAWINGS

The embodiments is now described, by way of example, with reference to the accompanying drawings, in which.

DETAILED DESCRIPTION OF PREFERRED EMBODIMENTS

Figure 1:
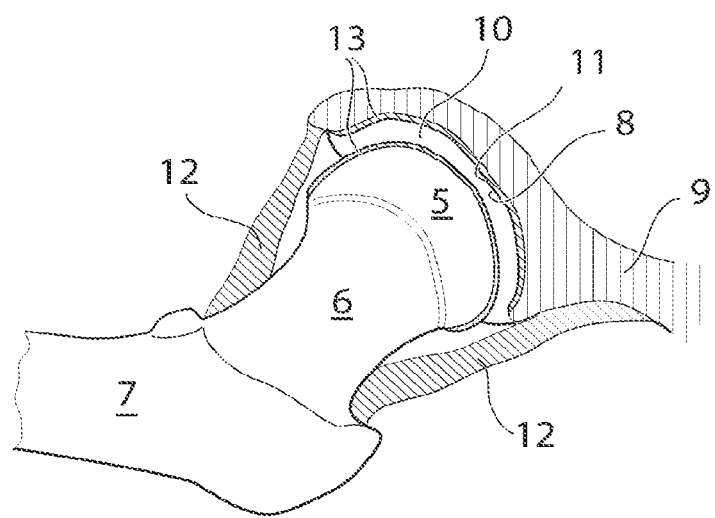
FIG. 1 shows the hip joint in section.

Biocompatible material is to be understood as being a material with low level of immune response. Biocompatible materials are sometimes also referred to as biomaterials. Analogous are biocompatible metals, metals with low immune response such as titanium or tantalum. The biocompatible metal could also be a biocompatible alloy comprising at least one biocompatible metal.

Elasticity is to be understood as a materials ability to deform in an elastic way.

Form fitting is to be understood as an element having a part or section which is adapted to enable a mechanical connection of said element to at least one other element using said part or section. Form fitted structure is a structure of an element which enables form fitting.

In the following a detailed description of preferred embodiments will be given. In the drawing figures, like reference numerals designate identical or corresponding elements throughout the several figures. It will be appreciated that these figures are for illustration only and are not in any way restricting the scope. Thus, any references to direction, such as "up" or "down", are only referring to the directions shown in the figures. Also, any dimensions etc. shown in the figures are for illustration purposes.

Required Steps Before the Placing of the Medical Device

FIG. 1 shows the hip joint of a human patient in section. The hip joint comprises a caput femur 5 which has a partly spherical shape with a diameter, the caput femur 5 is placed at the very top of collum femur 6 which is the top part of the femur bone 7. The caput femur is in connection with the acetabulum 8 which is a bowl shaped part of the pelvic bone 9. Both the caput femur surface 10 and the acetabulum surface 11 is covered with articular cartilage 13 which acts as a cushion in the hip joint. In patients with hip joint osteoarthritis, this articular cartilage 13 is abnormally worn down due to a low grade inflammation. The hip joint is surrounded by the hip joint capsule 12 which provides support for the joint and hinders luxation. After conventional hip joint surgery, penetrating the hip joint capsule 12, the capsule 12 is dramatically weakened due to the limited healing possibilities of its ligament tissue. By performing hip joint surgery without damaging the hip joint capsule 12 the patient can fully recover and place equal amount of strain on an artificial joint as is possible on a natural one.

Figure 2:
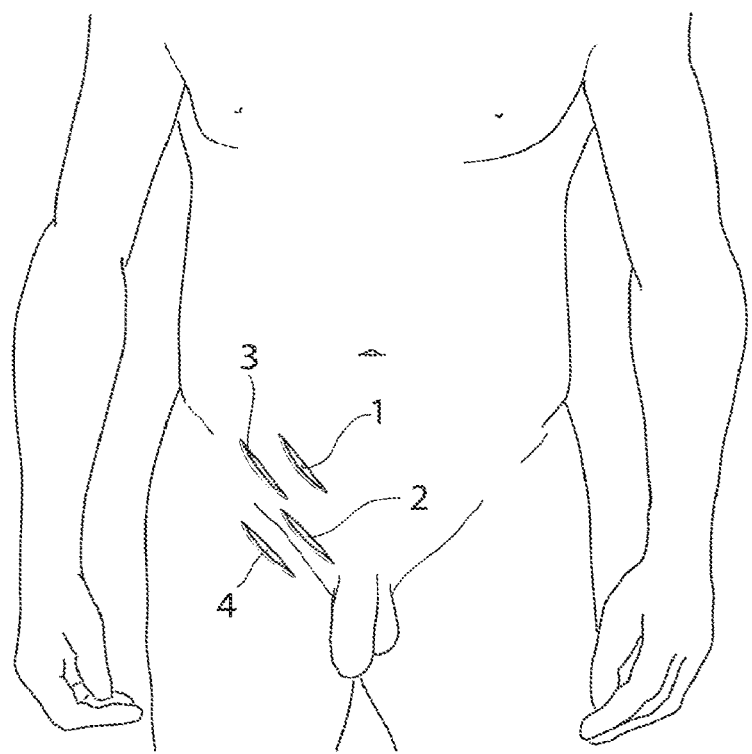
FIG. 2 shows different locations of the incisions made in the human body in the surgical method.

FIG. 2 shows a frontal view of the body of a human patient. A surgical method of operating the hip joint from the opposite side from acetabulum, is according to a first embodiment performed starting with an incision 1 in the abdominal wall of the human patient. The incision 1 passes through the abdominal wall, preferable rectus abdominis and peritoneum in to the abdomen of the human patient. In a second preferred embodiment the incision 2 is conducted in the abdominal wall, preferably through the rectus abdominis and in to the pelvic area, below peritoneum. According to a third embodiment the incision 3 is performed just between Illium of the pelvic bone and the surrounding tissue, an incision 3 which could enable the pelvic bone to be dissected with very little penetration of fascia and muscular tissue. According to a fourth embodiment the incision 4 is made in the inguinal region. In all of the four embodiments the tissue surrounding the pelvic bone 9 (FIG. 1) in the area opposite to acetabulum 8 (FIG. 1) is removed or penetrated or divided or moved away which enables the surgeon to reach the pelvic bone 9 (FIG. 1). It is obvious that the methods described may both be combined or altered reaching the same goal to dissect the pelvic bone on the opposite side of the acetabulum 8 (FIG. 1).

Figure 3:
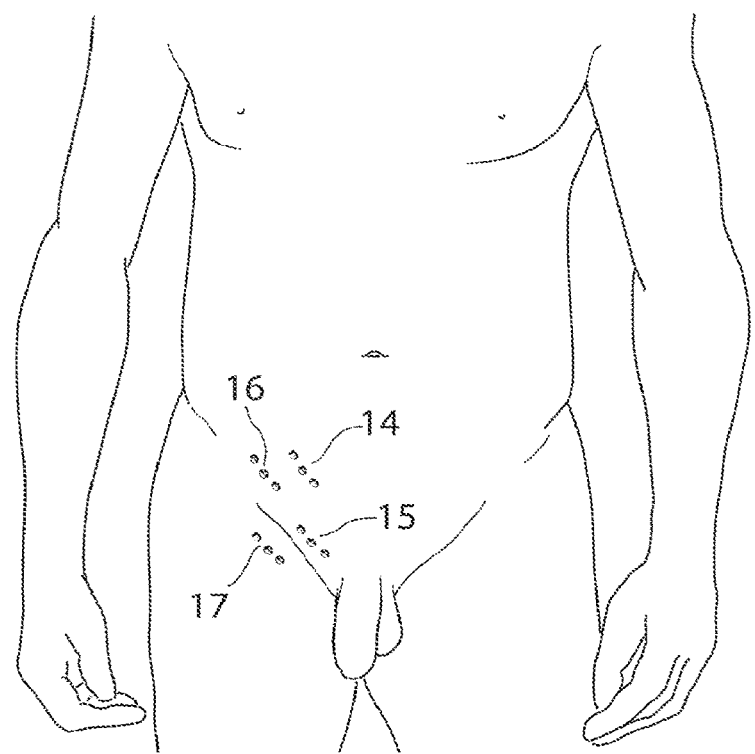
FIG. 3 shows different locations where small incisions can be made in the human body in the laparoscopic method.

FIG. 3 shows a frontal view of the body of a human patient. A laparoscopic method of operating the hip joint, from the opposite side from acetabulum, is according to a first embodiment performed starting with making small incisions 14 in the abdominal wall of the human patient. The small incisions enable the surgeon to insert laparoscopic trocars into the abdomen of the human patient. According to the first embodiment the incisions 14 passes through the abdominal wall, preferably rectus abdominis and peritoneum in to the abdomen of the human patient. According to a second preferred embodiment the small incisions 15 is conducted through the abdominal wall, preferably rectus abdominis and in to the pelvic area, below peritoneum. According to a third embodiment the small incisions 16 is performed just between Illium of the pelvic bone and the surrounding tissue, an incision 16 which could enable the pelvic bone to be dissected with very little penetration of fascia and muscular tissue. According to a fourth embodiment the incision 17 is made in the inguinal region. In all of the four embodiments the tissue surrounding the pelvic bone 9 (FIG. 1) in the area opposite to acetabulum 8 (FIG. 1) is removed or penetrated or divided or moved away which enables the surgeon to reach the pelvic bone 9 (FIG. 1).

Figure 4:
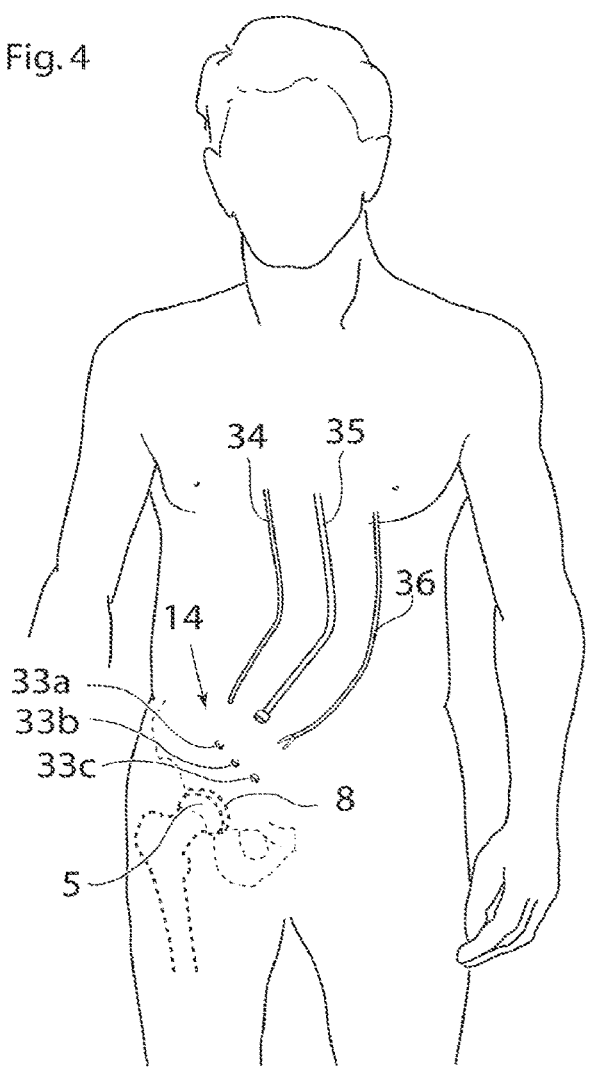
FIG. 4 shows the laparoscopic method of operating the hip joint of a human patient.

FIG. 4 shows a frontal view of the body of a human patient, illustrating the laparoscopic method of operating the hip joint from the opposite side from acetabulum 8. The hip joint comprising the acetabulum 8 and the caput femur 5. The small incisions 14 in the abdominal wall of the human patient allows the insertion of laparoscopic trocars 33a,b,c into the body of the patients. Whereafter one or more camera 34, a surgical instrument adapted to create a hole in the pelvic bone 35, or instruments 36 for dissecting, introducing, placing, connecting, attaching, creating or filling prosthesis or prosthetic parts, can be inserted into said body through said laparoscopic trocars 33a,b,c.

Figure 5:
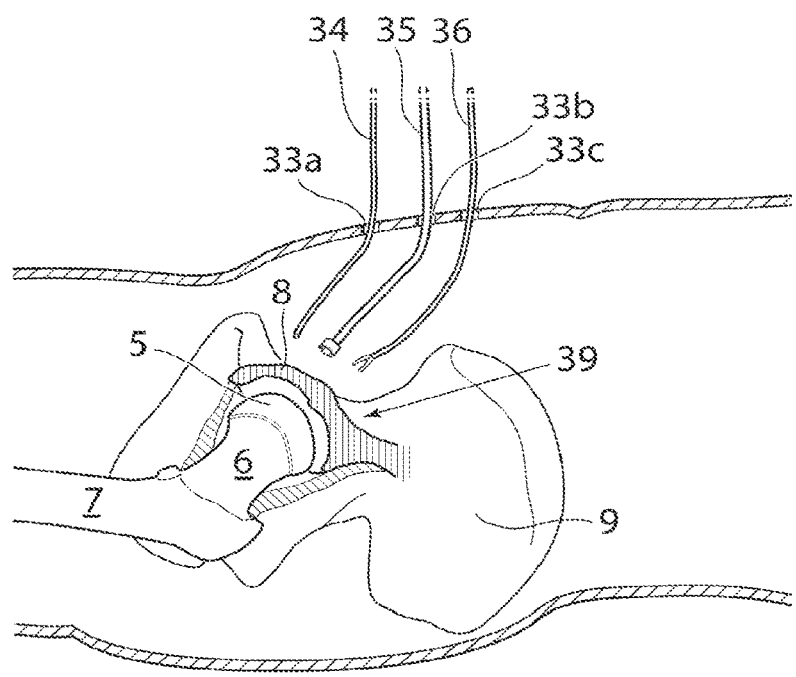
FIG. 5 shows a lateral view in section of the laparoscopic method.

FIG. 5 shows a lateral view of the body of a human patient, with the hip joint shown in section in further detail. The hip joint comprises a caput femur 5 placed at the very top of collum femur 6 which is the top part of the femur bone 7. The caput femur is in connection with the acetabulum 8 which is a bowl shaped part of the pelvic bone 9. Laparoscopic trocars 33a,b,c is being used to reach the hip joint 39 with one or more camera 34, a surgical instrument adapted to create a hole in the pelvic bone 35, or instruments 36 for dissecting, introducing, placing, connecting, attaching, creating or filling prosthesis or prosthetic parts.

Figure 6:
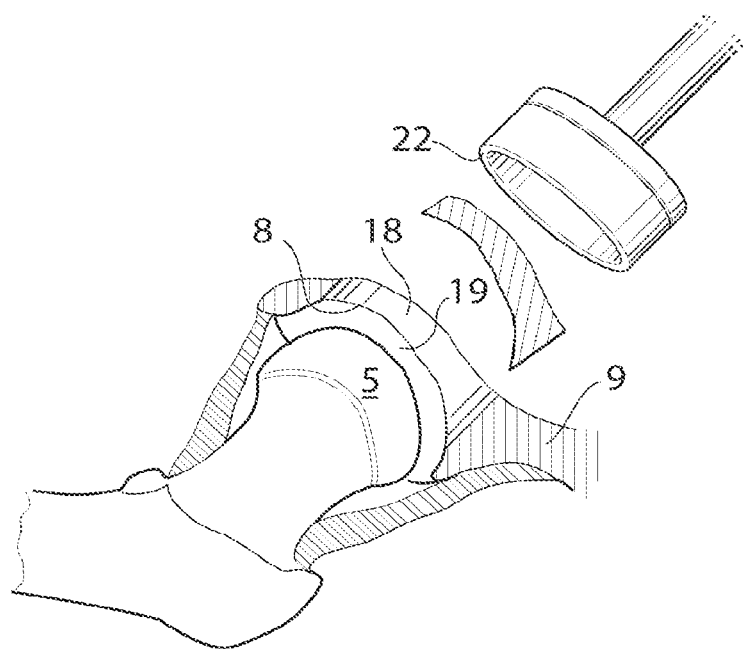
FIG. 6 shows the hip joint in section when a hole is created in the pelvic bone.

After dissecting the pelvic bone 9 a hole 18 is created in the bone 9, shown in FIG. 6. The hole 18 passes through the pelvic bone from the opposite side from acetabulum 8 and into the hip joint 39. The pelvic bone comprises an inner and outer cortex comprising cortical bone. Cortical bone is the outer, more sclerotic bone. The pelvic bone furthermore comprises a bone marrow comprising cancellous bone, which is more fragile.

FIG. 6 shows the hole 18 in the pelvic bone 9 according to a first embodiment, the hole 18 is large which allows prosthesis to pass through said hole 18 in their full functional size. The creation of a hole 18 creates edged of said hole 18 which comprises an inner cortex, on the abdominal side of the pelvic bone, and an outer cortex, on the acetabulum side of the pelvic bone 9.

Figure 7:
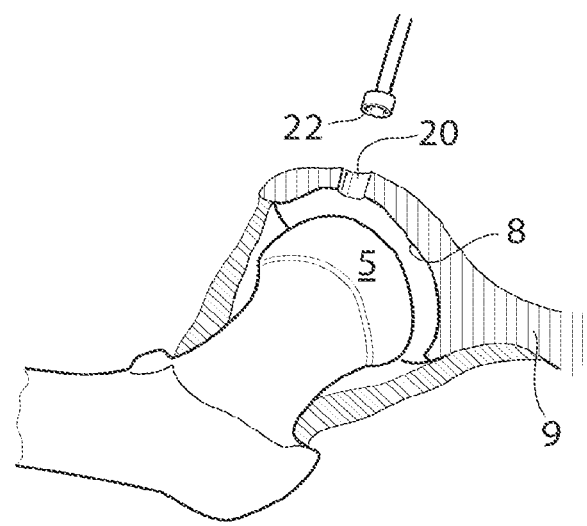
FIG. 7 shows the hip joint in section when a small hole is created in the pelvic bone.

FIG. 7 shows a second embodiment wherein the hole 20 created in the surgical or laparoscopic method is much smaller, which in turn allows the surgical 35 instrument (FIG. 5) creating the hole to be smaller, and thus the incision and dissection performed in the human body could be made smaller.

Before the medical device according to any of the embodiments can be provided, the hip joint surfaces could require preparation. The preparation could comprise reaming the acetabulum 8 and/or the caput femur 5.

Figure 8:
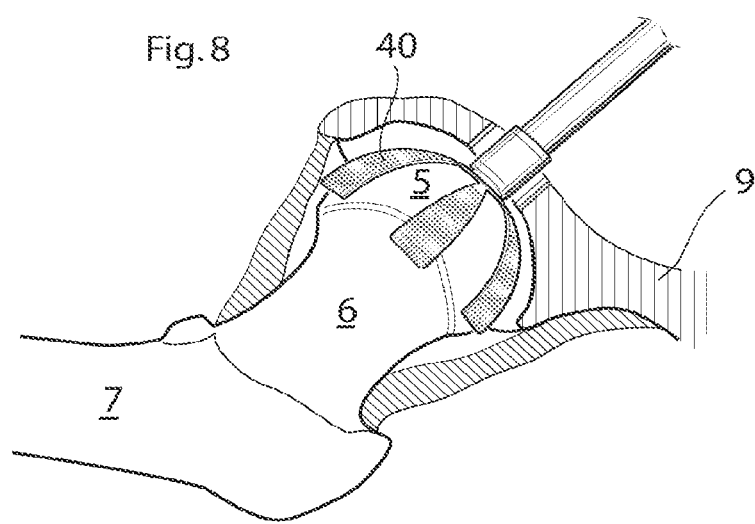
FIG. 8 shows the expandable reamer being used in the surgical or laparoscopic method.

FIG. 8 shows an expandable reamer reaming the acetabulum and/or the caput femur 5. The reamer can be adapted to be operated manually or by means of a rotating, vibrating or oscillating operating device. The reaming prepares the surfaces by removing some of the articular cartilage 13 which covers the contacting surfaces of the acetabulum 8 and the caput femur 5. The removing of the articular cartilage 13 creates room for a medical device comprising at least one hip joint surface, at the same time as it prepares the surfaces for the fixation of the medical device. The expandable reamer comprises multiple reaming blades 40 which in turn comprises abrasive elements or particles adapted to remove material of the hip joint when the expandable reamer is in use.

The Medical Device

According to one embodiment, after the preparation of the hip joint surfaces, a medical device comprising an artificial caput femur surface is provided.

Figure 9:
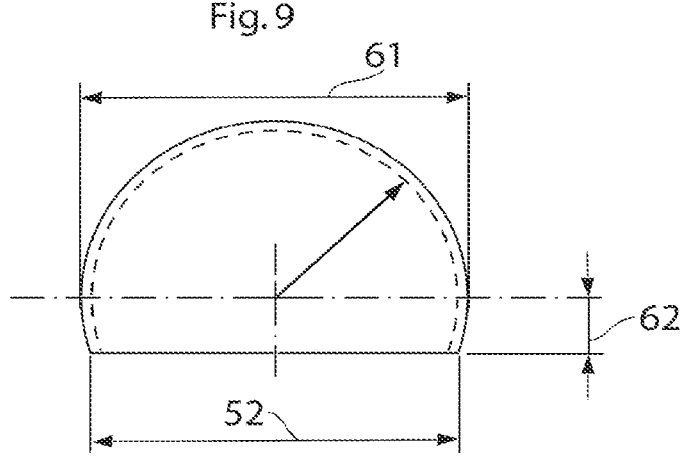
FIG. 9 shows an artificial caput femur surface being larger than equator frustum spherical.

FIG. 9 shows an artificial caput femur surface 45 in section having a greatest cross-sectional distance 52 adapted to travel over and beyond the maximum diameter of the caput femur 5. The largest diameter of the caput femur 5 being positioned at a corresponding largest cross sectional distance 61 of the artificial caput femur surface, a second distance 62 is the distance that the artificial caput femur surface 45 travels beyond the maximum diameter of the caput femur 5. Said distance 62 is the beyond part of the artificial caput femur surface and is a part of the mechanical fixation of the artificial caput femur surface 45 to the caput femur 5.

Figure 10:
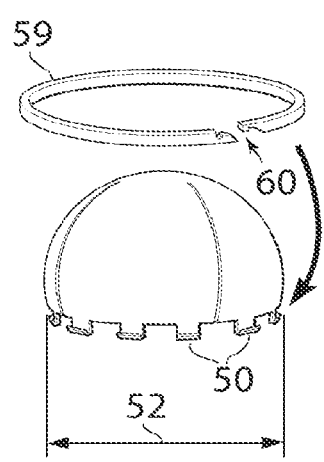
FIG. 10 shows the artificial caput femur surface according to a sixth embodiment.

FIG. 10 shows an artificial caput femur surface according to a first embodiment, the artificial caput femur surface 45 is adapted to pass beyond the maximum diameter of the caput femur 5. This enables a mechanical fixation using the form of said artificial caput femur surface 45. In this embodiment the artificial caput femur surface 45 comprises at least one slit 49 adapted to make said artificial caput femur surface 45 flexible for traveling over and beyond the maximum diameter of the caput femur 5. The construction could further be made flexible so that the size of the artificial caput femur surface 45 can vary to become smaller for insertion through a hole 18 in the pelvic bone 9 smaller than the full functional size of the artificial caput femur surface 45. It is also conceivable that the artificial caput femur surface 45 comprises two or more artificial caput femur surface arms 50 which have a cross sectional distance 52 between each other. This cross sectional distance 52 is according to one embodiment shorter than the maximum diameter of the caput femur 5 enabling the mechanical fixation of the artificial caput femur surface 45 by means of said artificial caput femur surface arms 50. For further fixation a band, cord or wire 59 can be placed around the artificial caput femur surface 45 beyond the maximum diameter of the caput femur 5. The band, cord or wire can be mechanically connected using a self locking member 60 for forming a ring-shaped element able to assist in the fixation of the artificial caput femur surface 45 to the caput femur 5.

Figure 11:
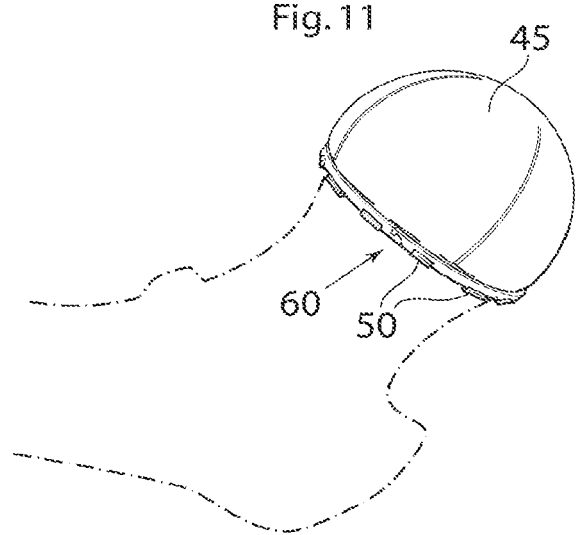
FIG. 11 shows the artificial caput femur surface according to a sixth embodiment when fixated to the caput femur.

FIG. 11 shows the artificial caput femur surface 45 when fixated to the caput femur with the supporting band, cord or wire placed around the artificial caput femur surface 45 beyond the maximum diameter of the caput femur 5. The arms may also be adapted to go into the bone of caput femur 5 to lock said artificial caput femur surface 45.

Figure 12:
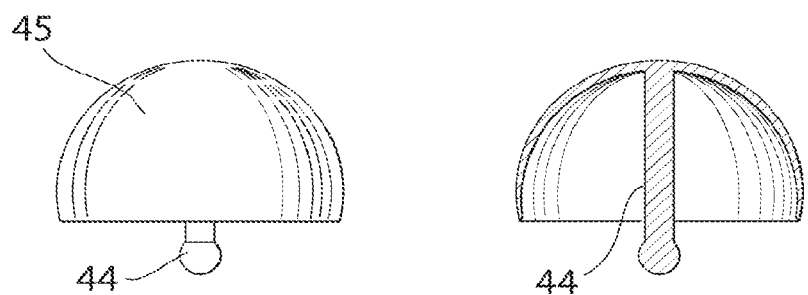
FIG. 12 shows the artificial caput femur surface according to a first embodiment.

FIG. 12 shows the artificial caput femur surface 45 according to one embodiment. The shaft or screw placed in the middle of the artificial caput femur surface 45 serves as a mechanical attachment 44 penetrating the cortex of the caput femur 5 and fixating the artificial caput femur surface 45 to the caput femur 5. However it is also conceivable that said shaft or screw is assisted or replaced with screws, welding, sprints, band, adhesive or some other mechanical connecting member.

Figure 13:
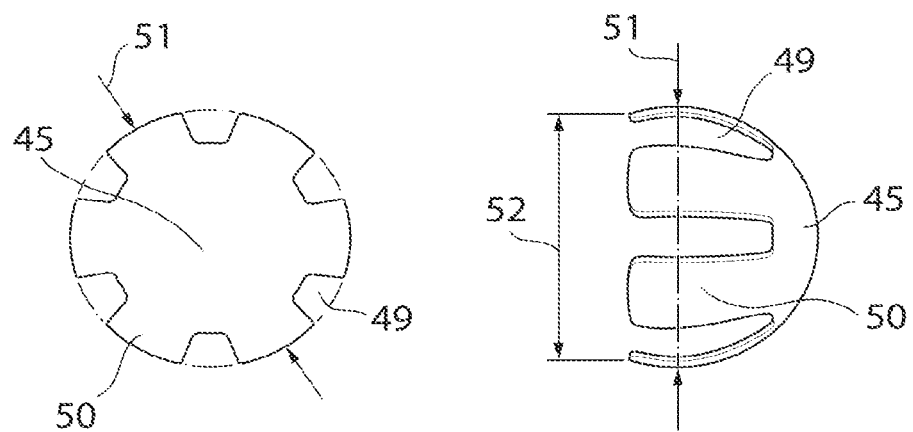
FIG. 13 shows the artificial caput femur surface according to a second embodiment.

FIG. 13 shows the artificial caput femur surface 45 according to another embodiment, in which said artificial caput femur surface 45 comprises at least one slit 49 enabling the construction of the artificial caput femur surface 45 to be flexible, thus enabling the largest diameter 51 to vary for insertion of said artificial caput femur surface 45 through a hole in the pelvic bone 9 smaller than the full functional size of said artificial caput femur surface 45. According to this embodiment the artificial caput femur surface 45 further comprises artificial caput femur surface arms 50 located on the sides of said at least one slit 49. The caput femur surface arms 50 can be made of a flexible material enabling the insertion through a hole 20 in the pelvic bone 9 smaller than the largest diameter 51 of said artificial caput femur surface 45 when in its full functional size.

According to one embodiment the artificial caput femur surface 45 of said third embodiment could be adapted to pass beyond the maximum diameter of the caput femur 5. This enables a mechanical fixation using the form of said artificial caput femur surface 45. In the embodiment where the artificial caput femur surface 45 travels beyond the maximum diameter of the caput femur 5 the construction can be made flexible so that the size of the artificial caput femur surface 45 can vary to become smaller for insertion through a hole 18 in the pelvic bone smaller than the full functional size of the artificial caput femur surface 45, and have an opening adapter to travel over the caput femur 5 that can be larger that the same opening is in the full functional size of the artificial caput femur surface 45 enabling the artificial caput femur surface 45 to at least partly cover an area beyond the maximum diameter of caput femur 5 from the direction of the acetabulum 8. According to a second embodiment the artificial caput femur surface 45 comprises two or more artificial caput femur surface arms 50 which have a cross sectional distance 52 between each other. This cross sectional distance 52 is according to one embodiment shorter than the maximum diameter of the caput femur 5 enabling the mechanical fixation of the artificial caput femur surface 45 by means of said artificial caput femur surface arms 50.

Figure 14A:
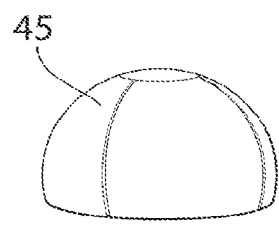
FIG. 14a-14e shows the artificial caput femur surface according to a third embodiment.
Figure 14B:
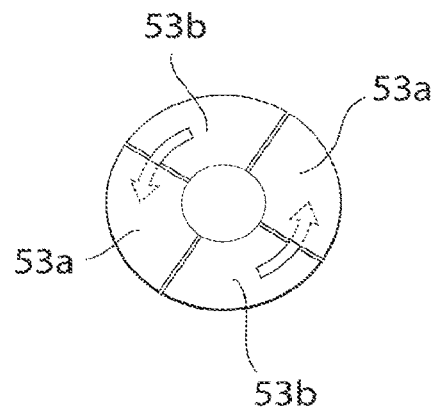
Figure 14C:
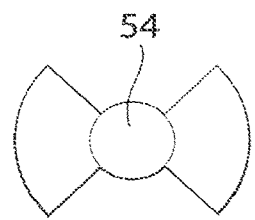
Figure 14D:
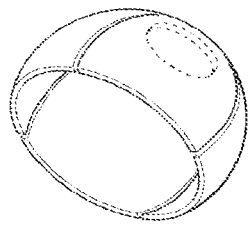
Figure 14E:
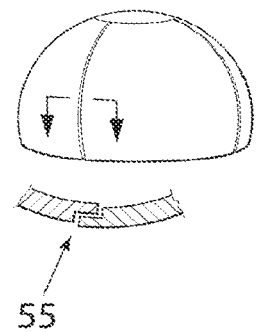

FIG. 14*a,b,c,d,e* shows the artificial caput femur surface 45 according to a fourth embodiment, in which said artificial caput femur surface 45 comprises a first 53*a* and a second 53*b* section, as shown in FIG. 14*b*. The first and second sections are displaceable in relation to each other. According to a first embodiment said first section 53*a* can be rotated in relation to said second section 53*b* so that said second section 53*b* travels underneath said first section 53*a* to create a displaced artificial caput femur surface 54, as shown in FIG. 14*c*, which is possible to insert into a hip joint of a human patient through a hole 18 being oval, or at least having an area smaller than the cross sectional area of the artificial caput femur surface 45 when in its full functional size 45, as shown in FIG. 14*a*. According to this embodiment the two sections are connected to each other when the artificial caput femur surface 45 is returned to its full functional size using a mechanical form fitting 55, as shown in FIG. 14*e*. However it is also conceivable that said connection is assisted or replaced with screws, welding, sprints, band, adhesive or some other mechanical connecting member.

Figure 15A:
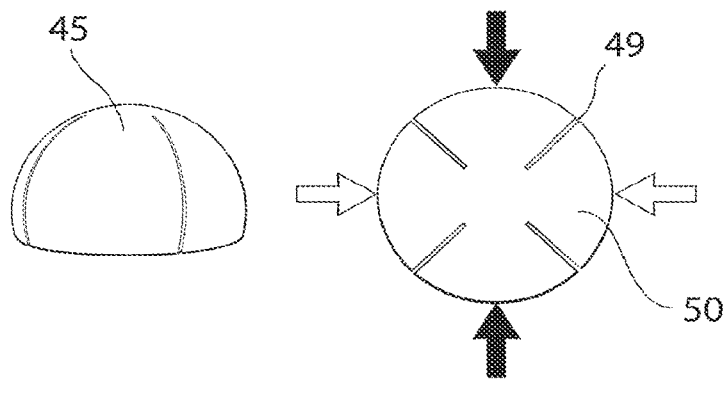
FIG. 15a shows the artificial caput femur surface according to a fourth embodiment.

FIG. 15*a,b* shows the artificial caput femur surface 45 according to another embodiment, in which said artificial caput femur surface 45 comprises four slits. The artificial caput femur surface 45 is flexible in its construction allowing the four artificial caput femur arms 50 to be folded towards the center axis of the artificial caput femur surface 45 thus allowing the artificial caput femur surface 45 to be inserted into a hip joint through a hole smaller than the full functional size of the artificial caput femur surface 45. The artificial caput femur surface 45 according to this embodiment can be constructed to go beyond the maximum diameter of the caput femur 5, in which case the construction with the slits 49 allows the artificial caput femur surface 45 to change to both a smaller and a larger size than said full functional size.

Figure 15B:
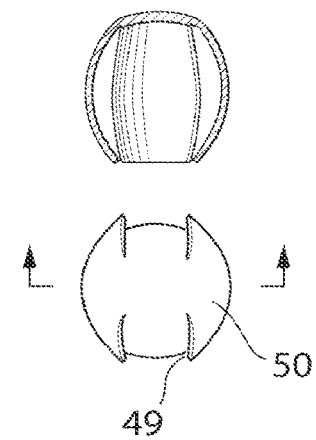
FIG. 15b shows the artificial caput femur surface according to the fourth embodiment in its folded state.

FIG. 15*b* shows the artificial caput femur surface 45 in section when said artificial caput femur surface arms 50 are folded for insertion through a hole 18 with an area smaller than the largest area of the artificial caput femur surface 45 when in its full functional size.

Figure 16A:
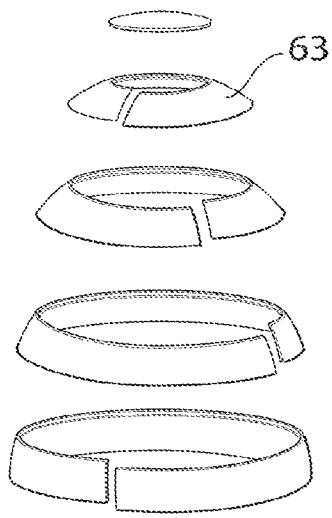
FIG. 16a shows the artificial caput femur surface according to a seventh embodiment.
Figure 16B:
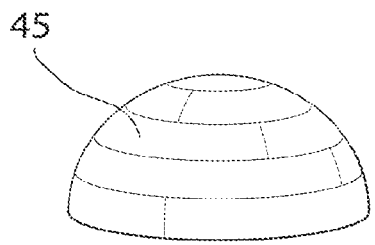
FIG. 16b shows the artificial caput femur surface according to the seventh embodiment when assembled.
Figure 16C:
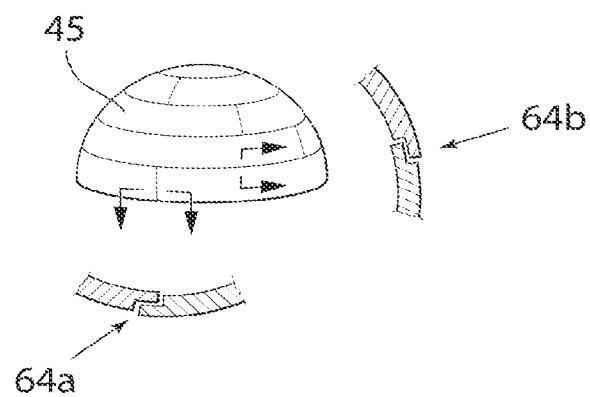
FIG. 16c shows the artificial caput femur surface according to the seventh embodiment with the connecting members enlarged.

FIG. 16*a* shows the artificial caput femur surface 45 according to a sixth embodiment, in which said artificial caput femur surface 45 comprises multiple ring-shaped artificial caput femur surface parts 63. Said multiple ring-shaped artificial caput femur surface parts 63 are adapted to be connected to each other to form an artificial caput femur surface 45, shown in FIG. 16*b*. According to one embodiment said artificial caput femur surface parts 63 are adapted to be connected to each other using mechanical connecting members 64*a,b*. In FIG. 16*c*, 64*a* shows how an individual ring-shaped artificial caput femur surface part 63 can be connected to itself to form a continuous ring shape. 64*b* shows how an individual ring-shaped artificial caput femur surface part 63 connects to other ring-shaped artificial caput femur surface parts 63 to form an artificial caput femur surface 45. The artificial caput femur surface 45 according to this embodiment can further be adapted to go beyond the maximum diameter of the caput femur 5.

Figure 17A:
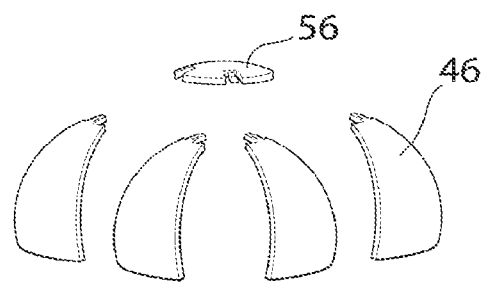
FIG. 17a shows the artificial caput femur surface according to a fifth embodiment.
Figure 17B:
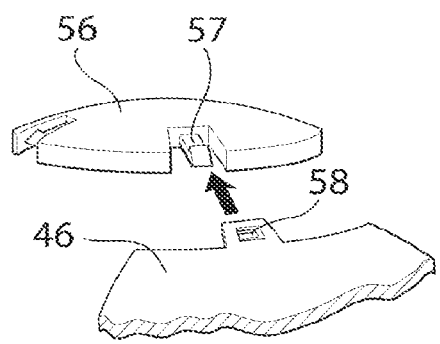
FIG. 17b shows the artificial caput femur surface according to the fifth embodiment in greater detail.
Figure 17C:
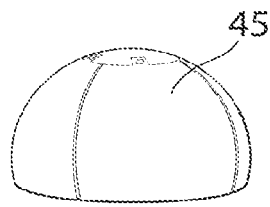
FIG. 17c shows the artificial caput femur surface according to the fifth embodiment when assembled.

FIG. 17a,b,c shows the artificial caput femur surface 45 according to a sixth embodiment, in which said artificial caput femur surface 45 comprises multiple artificial caput femur surface parts 46. Said multiple artificial caput femur surface parts 46 are adapted to be connected to an interconnecting artificial caput femur surface part 56 after insertion into a hip joint. The interconnecting artificial caput femur surface part 56, which serves as a base part, comprises self locking connecting members 57, shown in FIG. 17b, that fits with corresponding self locking members 58 of the artificial caput femur surface parts 46. The artificial caput femur surface parts 46 create an artificial caput femur surface 45 when connected to each other, shown in FIG. 17c. The self locking members 57, 58 can be assisted or replaced with screws, welding, sprints, band, adhesive or some other mechanical connecting member. The artificial caput femur surface 45 according to this embodiment can further be adapted to go beyond the maximum diameter of the caput femur 5.

Figure 18:
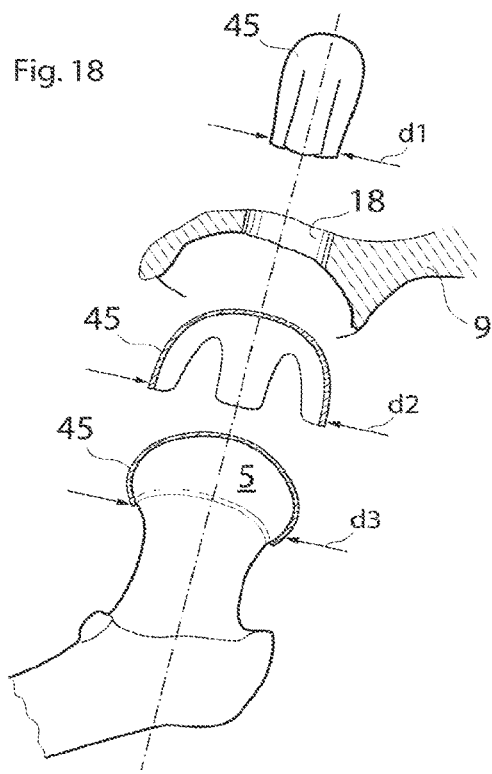
FIG. 18 shows a conceptual view of the function of the expandable caput femur surface.

FIG. 18 shows a conceptual way wherein the artificial caput femur surface 45 has a diameter or cross-sectional distance d1 small enough to enable said artificial caput femur surface 45 to travel through a hole 20 in the pelvic bone 9. After the artificial caput femur surface 45 has traveled through the hole 20 in the pelvic bone 9 the artificial caput femur surface 45 is expanded such that the diameter or cross-sectional distance d2 is large enough to travel over the caput femur 5. Finally the artificial caput femur surface 45 is positioned on the caput femur 5, in this state the diameter or cross-sectional distance is smaller than the largest diameter of the caput femur 5 which mechanically attaches the artificial caput femur surface 45 to the caput femur 5. d3 is the normal state cross sectional distance of the medical device, i.e. the cross sectional distance that the medical device has when the medical device is in its functional position. This figure may also in an alternative embodiment show the artificial acetabulum surface mounted onto caput femur or an artificial replacement therefore with the same locking principle.

Figure 19A:
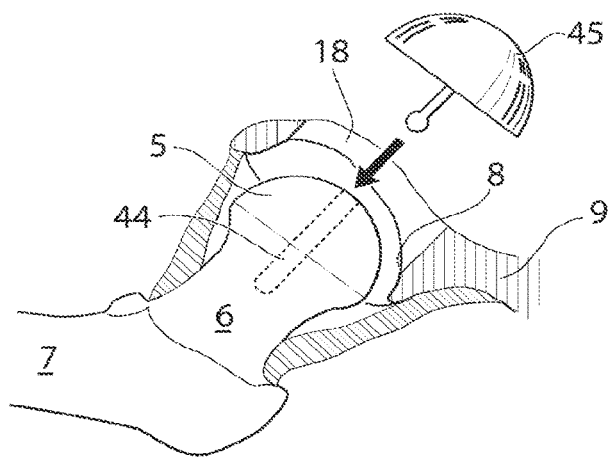
FIG. 19a shows the step of providing an artificial caput femur surface.
Figure 19B:
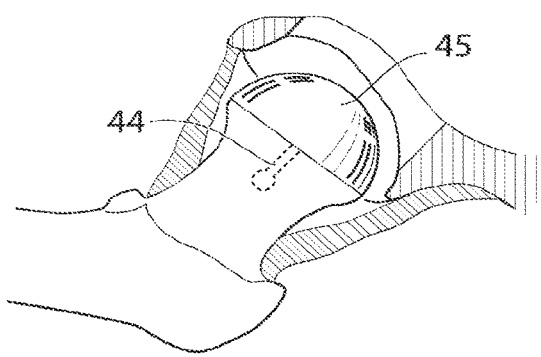
FIG. 19b shows a section of the hip joint after the artificial caput femur surface has been provided.

FIG. 19a,b shows the hip joint in section with the caput femur 5 placed at the very top of collum femur 6, which is the top part of the femur bone 7. The caput femur is in connection with the acetabulum 8, which is a bowl shaped part of the pelvic bone 9. According to a first embodiment the hole 18 created in the pelvic bone 9 from the opposite side from acetabulum 8, is larger than said artificial caput femur surface 45, enabling the insertion of said artificial caput femur surface 45 in its full functional size. Said insertion of said artificial caput femur surface 45 could be performed as a step of the surgical method, as well as a step of the laparoscopic method. After the insertion, the artificial caput femur surface 45 is attached to the caput femur 5, the attaching is performed by means of a mechanical attachment 44 comprising a shaft or screw penetrating the cortex. It is however also conceivable that the mechanical attachment 44 is assisted or replaced by bone cement or adhesive placed between caput femur 5 and the artificial caput femur surface 45, or in connection with said shaft or screw 44. Alternative ways of attaching the artificial caput femur surface 45 includes: at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members. FIG. 19b shows the hip joint in section with the artificial caput femur surface 45 attached to the caput femur 5.

Figure 20A:
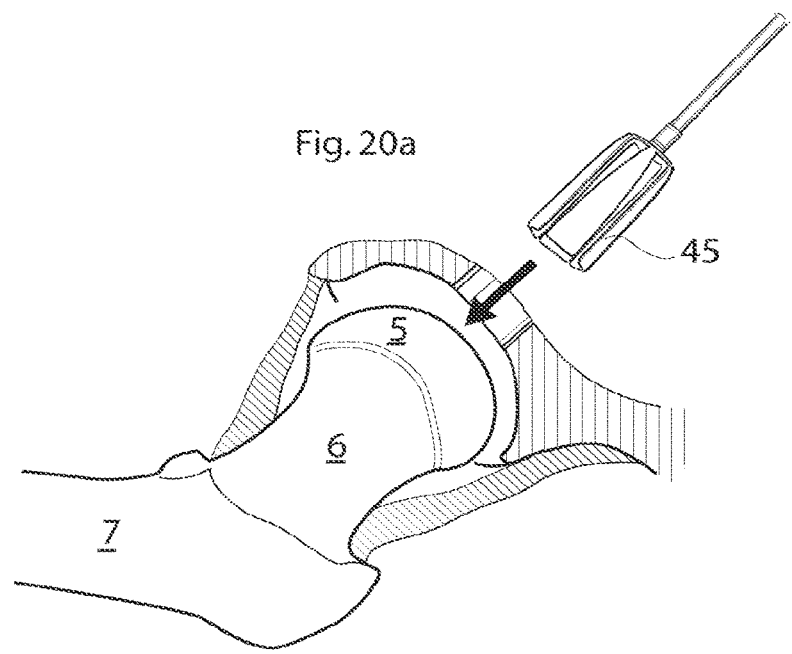
FIG. 20a shows an expandable artificial caput femur surface, according to the second embodiment, when travelling through a hole in the pelvic bone.

FIG. 20a shows how an expandable artificial caput femur surface 45 is being inserted through a hole 18 in the pelvic bone 9.

Figure 20B:
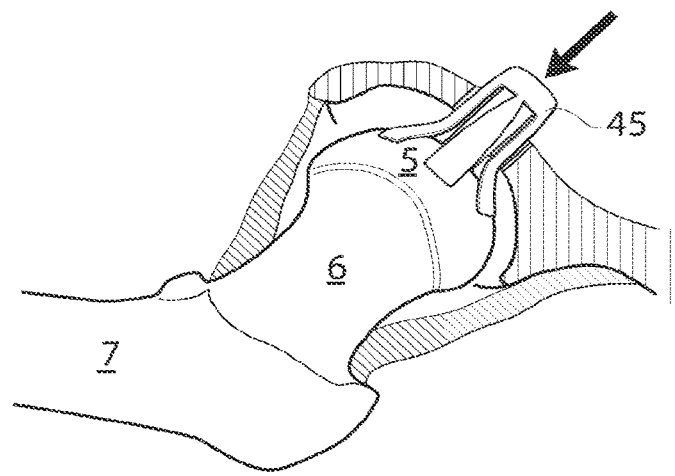
FIG. 20b shows an expandable artificial caput femur surface, according to the second embodiment, when being placed on the caput femur.

FIG. 20b shows how an expandable artificial caput femur surface 45 travels through the hole 18 in the pelvic bone 9 and travels over caput femur 5.

Figure 20C:
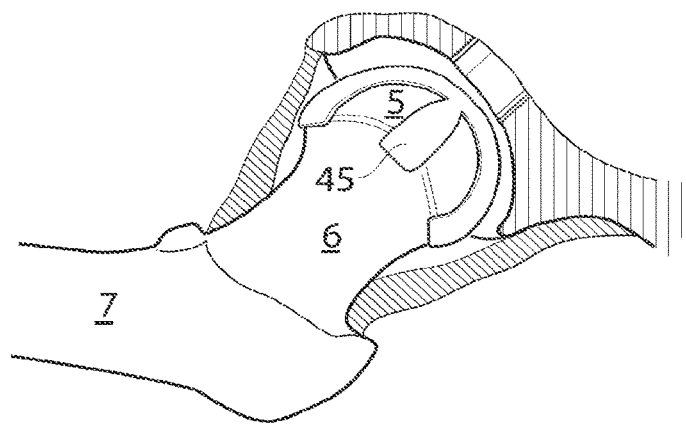
FIG. 20c shows an expandable artificial caput femur surface, according to the second embodiment, when placed on the caput femur.

FIG. 20c shows an expandable artificial caput femur surface 45 is after it has been placed on said caput femur 5.

Figure 21A:
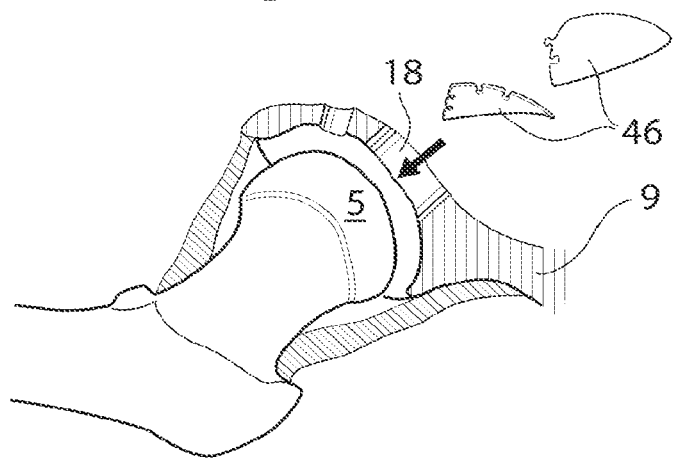
FIG. 21a show the insertion of artificial caput femur surface parts into the hip joint.

FIG. 21a shows the hip joint in section according to a second embodiment in which the hole 18 in the pelvic bone 9 is smaller than the artificial caput femur surface 45 in its full functional size. According to this embodiment the artificial caput femur surface 45 is introduced into said hip joint through the hole 18 in the pelvic bone 9 form the opposite side from acetabulum 8. The artificial caput femur surface parts 46 are connected to each other after insertion into said hip joint to form the artificial caput femur surface 45.

Figure 21B:
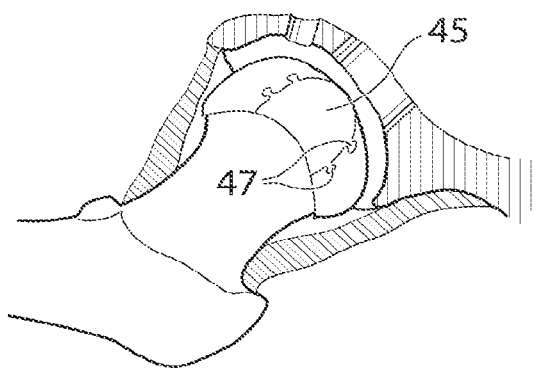
FIG. 21b shows the artificial caput femur surface parts after they have been connected inside of the hip joint forming an artificial caput femur surface.

FIG. 21b shows the hip joint in section when the artificial caput femur surface parts 46 are connected to each other using form fitting 47, however it is conceivable that the form fitting is assisted or replaced with adhesive or bone cement. After the artificial caput femur surface parts 46 have been introduced and connected in the hip joint, they are mechanically fixated to the caput femur 5, the mechanical fixation could be done by means of: at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members.

Figure 21D:
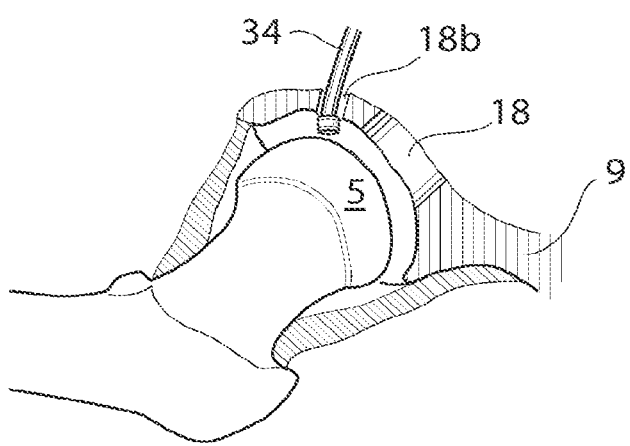
FIG. 21d shows the hip joint in section when a second hole for a camera is provided.
Figure 21C:
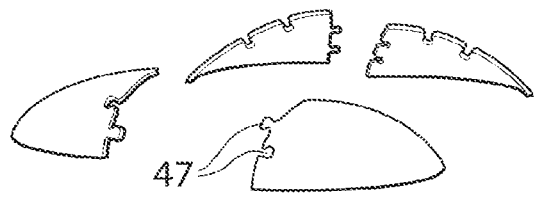
FIG. 21c shows how the form of the artificial caput femur surface parts enables the connection of the artificial caput femur surface parts to form an artificial caput femur surface.

FIG. 21c shows the artificial caput femur surface parts 46 with the parts supplying the form fitting 47.

FIG. 21d shows the hip joint in section wherein a second hole 18b in the pelvic bone 9 enables the surgeon to place a camera 34 into the hip joint, preferably used in the laparoscopic method.

According to one embodiment the medical device comprises an artificial acetabulum surface 65. In the embodiments where the medical device comprises an artificial caput femur surface 45 and an artificial acetabulum surface 65, the artificial acetabulum surface is provided after the artificial caput femur surface.

Figure 22:
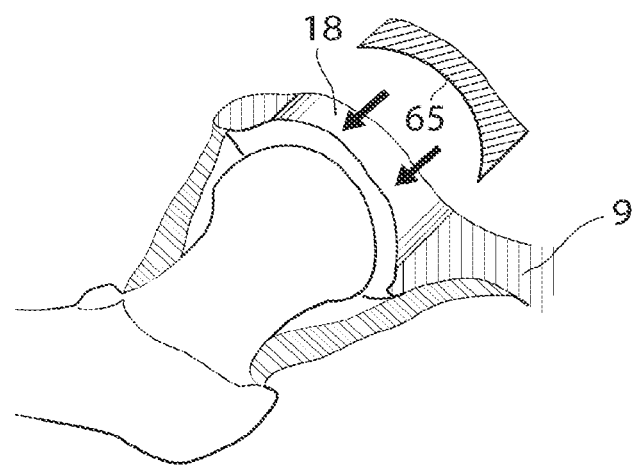
FIG. 22 shows an artificial acetabulum surface when being inserted into a hip joint.

FIG. 22 shows an artificial acetabulum surface 65 in its full functional size, as it is being inserted through a hole 18 in the pelvic bone 9. The hole being large enough to allow the artificial acetabulum surface to pass through the hole.

Figure 23A:
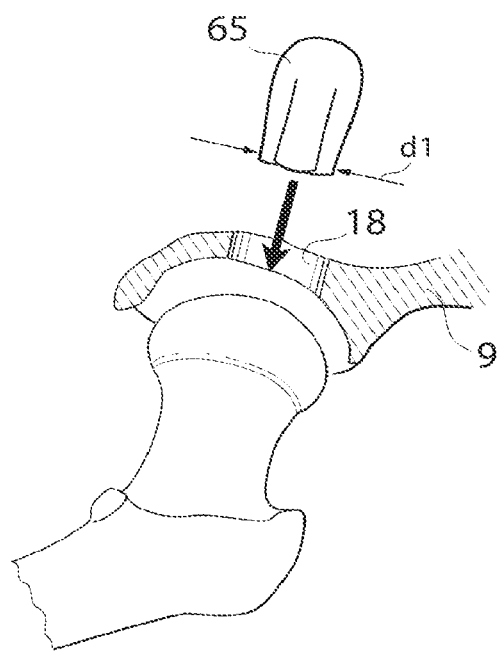
FIG. 23a shows a conceptual view of the function of the expandable acetabulum surface.

FIG. 23a shows an artificial acetabulum surface in a conceptual way, wherein the artificial acetabulum surface 65 has a diameter or cross-sectional distance d1 small enough to enable said artificial acetabulum surface 65 to travel through a hole 18 in the pelvic bone 9. After the artificial acetabulum surface 65 has traveled through the hole 18 in the pelvic bone 9, the artificial acetabulum surface is expanded such that the diameter or cross-sectional distance d2 is large enough to hinder the artificial acetabulum surface 65 from traveling through the hole 18 in the pelvic bone 9.

Figure 23B:
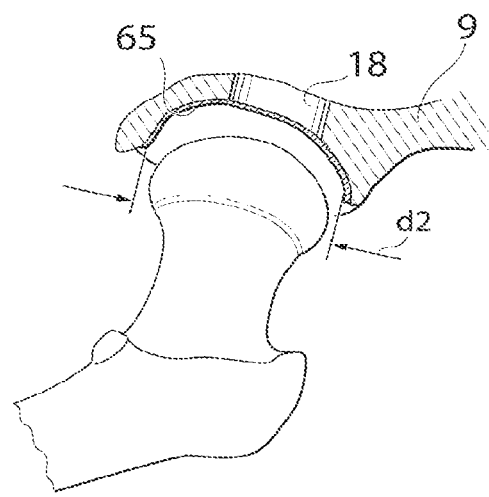
FIG. 23b shows the expandable acetabulum surface when positioned.

FIG. 23b shows the artificial acetabulum surface 65 when positioned in the acetabulum 8.

Figure 24:
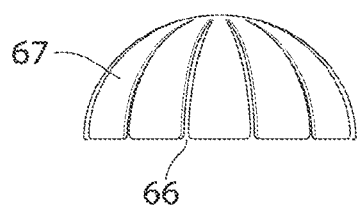
FIG. 24 shows an artificial acetabulum surface according to a first embodiment.
Figure 24:
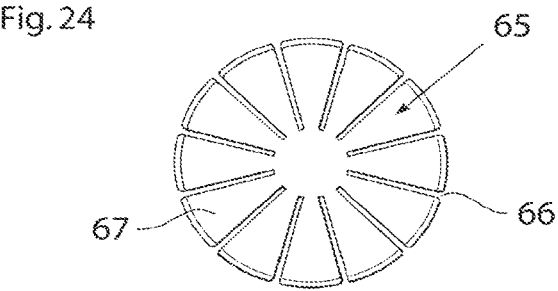

FIG. 24 shows an artificial acetabulum surface 65 according to a second embodiment in which the artificial acetabulum surface 65 comprises at least one slit 66 enabling the artificial acetabulum surface 65 to vary in size for insertion through a hole 18 in the pelvic bone 9 smaller than the full functional size of the artificial acetabulum surface 65. The slits are placed between one or more artificial acetabulum surface arms 67 which are flexible by means of the material or by means of a joint affecting said artificial acetabulum surface arms 67.

Figure 25A:
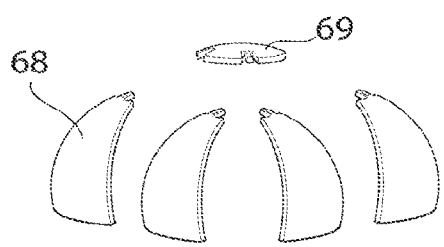
FIG. 25a shows an artificial acetabulum surface according to a second embodiment.
Figure 25B:
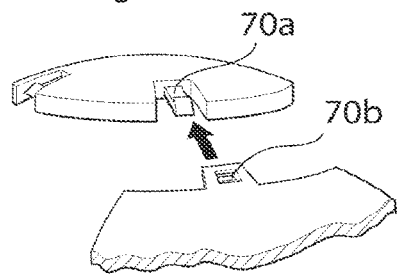
FIG. 25b shows an artificial acetabulum surface according to the second embodiment in greater detail.
Figure 25C:
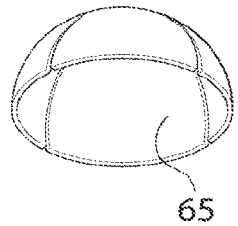
FIG. 25c shows the artificial acetabulum surface when assembled.

FIG. 25a,b,c shows an artificial acetabulum surface 65 according to a second embodiment in which the artificial acetabulum surface 65 comprises multiple artificial acetabulum surface parts 68. Said multiple artificial acetabulum surface parts 68 are adapted to be connected to an interconnecting artificial acetabulum surface part 69 after insertion into a hip joint. The interconnecting artificial caput femur surface part 69 comprises self locking connecting members 70a, shown in FIG. 25b, that fits with corresponding self locking members 70b of the artificial acetabulum surface parts 68. The artificial acetabulum surface parts 68 create an artificial acetabulum surface 65 when connected to each other, shown in FIG. 25c. The self locking members 70a,b can be assisted or replaced with at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members.

Figure 26A:
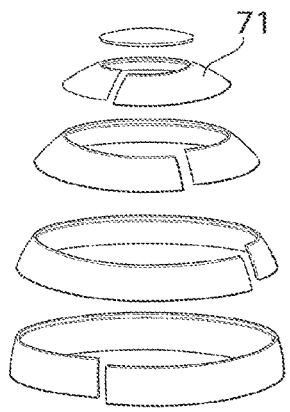
FIG. 26a shows an artificial acetabulum surface according to one embodiment.
Figure 26B:
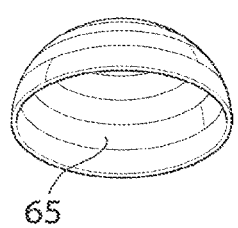
FIG. 26b shows an artificial acetabulum surface according to one embodiment when assembled.

FIG. 26a,b,c shows an artificial acetabulum surface 65 according to a third embodiment in which the artificial acetabulum surface 65 comprises multiple ring-shaped artificial acetabulum surface parts 71. Said multiple ring-shaped artificial acetabulum surface parts 71 are adapted to be connected to each other to form an artificial acetabulum surface 65 after insertion in a hip joint. According to one embodiment said artificial acetabulum surface parts 71 are adapted to be connected to each other using mechanical connecting members 72a,b.

Figure 26C:
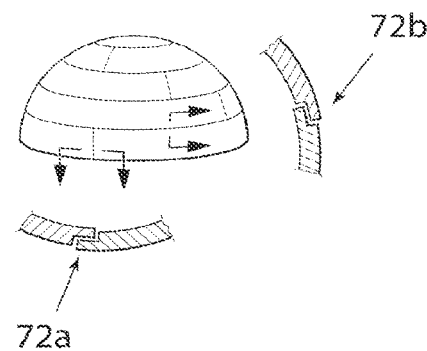
FIG. 26c shows the connection function of the artificial acetabulum surface according to the embodiment of FIGS. 26a and 26b.

FIG. 26c shows how an individual ring-shaped artificial acetabulum surface part 71 can be connected to itself using the mechanical connecting member 72a to form a continuous ring shape. Further 37c shows how an individual ring-shaped artificial acctabulum surface part 71 connects to other ring-shaped artificial acctabulum surface parts 71 using the mechanical connecting member 72b to form an artificial acetabulum surface 65.

Figure 27A:
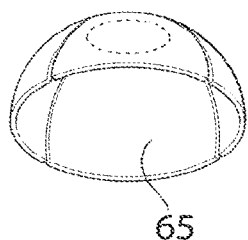
FIG. 27a shows an artificial acetabulum surface according to a fourth embodiment.
Figure 27B:
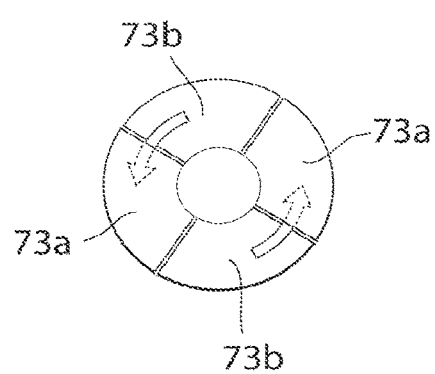
FIG. 27b shows the function of the artificial acetabulum surface according to the fourth embodiment.
Figure 27C:
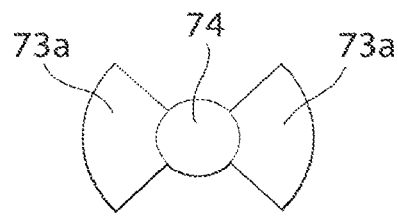
FIG. 27c shows an artificial acetabulum surface according to a fourth embodiment in its folded state.
Figure 27D:
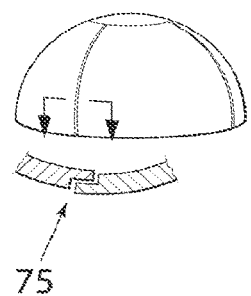
FIG. 27d shows an artificial acetabulum surface according to a fourth embodiment in perspective.

FIG. 27a,b,c,d shows an artificial acetabulum surface 65 according to a fourth embodiment in which the artificial acetabulum surface 65 comprises a first 73a and a second 73b section, shown in FIG. 27b. The first and second sections are displaceable in relation to each other. According to one embodiment said first section 73a can be rotated in relation to said second section 73b so that said second section 73b travels underneath said first section 73a to create a displaced artificial acetabulum surface 74, as shown in FIG. 27c, which is possible to insert into a hip joint of a human patient through a hole being oval, or at least having an area smaller than the cross sectional area of the artificial acetabulum surface 65 when in its full functional size 65. According to this embodiment the two sections 73a,b are connected to each other when the artificial acetabulum surface is returned to its full functional size using a mechanical form fitting 75, as shown in FIG. 27d. However it is also conceivable that said connection is assisted or replaced with at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members.

Figure 28A:
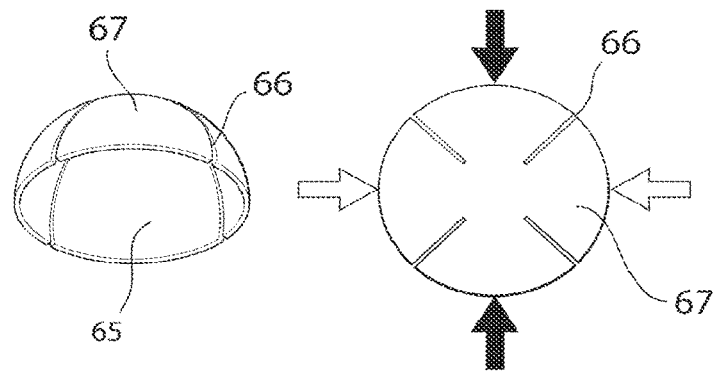
FIG. 28a shows an artificial acetabulum surface according to a fifth embodiment.

FIG. 28a shows an artificial acetabulum surface 65 according to a fifth embodiment in which the artificial acetabulum surface 65 comprises four slits 66. The artificial acetabulum surface 65 is flexible in its construction allowing the four artificial acetabulum arms 67 to be folded towards the center axis of the artificial acetabulum surface 65 thus allowing the artificial acetabulum surface to be inserted into a hip joint through a hole smaller than the full functional size of the artificial acetabulum surface 65.

Figure 28B:
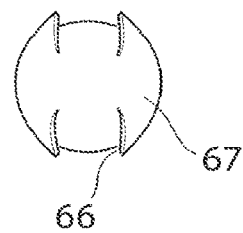
FIG. 28b shows an artificial acetabulum surface according to the fifth embodiment in its folded state.

FIG. 28b shows the artificial acetabulum surface 65 according to the fifth embodiment in its folded state.

After the medical device, comprising at least one hip joint surface, has been provided through a hole 18 in the pelvic bone 9, in accordance with any of the embodiment above, said hole 18 needs to be closed. The hole can be closed using the medical device, however it is also conceivable that closing of the hole is performed with assistance of an additional prosthetic part, or a piece of human bone. In the embodiments where the closing is assisted by a piece of human bone, that piece could simply be the piece drilled from the pelvic bone or a modified piece from the pelvic bone e.g. equipped with additional supporting members.

Figure 29A:
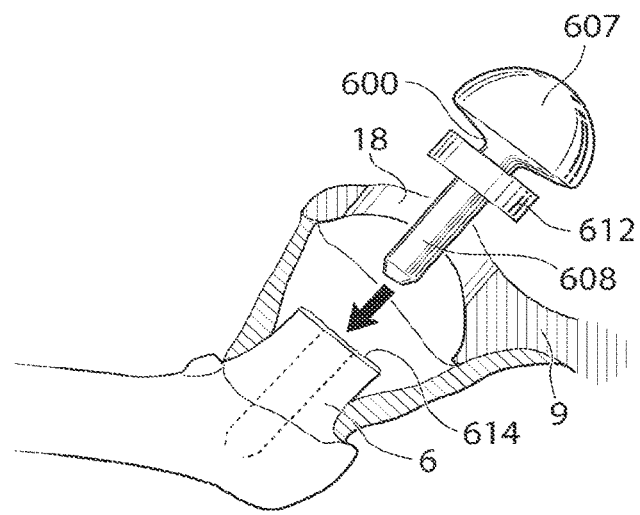
FIG. 29a-c shows the closing of a hole in the hip joint using a bone plug, FIG. 30a,b shows the fixation of a bone plug in the pelvic bone.

FIG. 29a shows an embodiment where a solid medical device 600 is fixated to the collum femur 6, introduced through a hole 18 in the pelvic bone 9. The stabilizing member 612 is adapted to stabilize the medical device 600 from the outside of the collum femur 6 substantially perpendicular to the longitudinal extension of the collum femur 6, and from the acetabulum side, substantially in line with the longitudinal extension of the collum femur 6 through the stabilizing member being placed in contact with the outside of the collum femur 6 and the surface of the section 610 in the collum femur 6. The stabilizing member is fixated to the outside of the collum femur and/or to the surface of the section in the collum femur by means of the adhesive 614. However the adhesive 614 could be replaced or assisted by bone cement or a mechanical fixation element 615. The medical device 600 has a smallest passable area being an area of a hole 18 through which the medical device 600 can pass. To enable the solid medical device 607 to pass through said hole in the pelvic bone the solid medical device 600 is smaller than the caput femur, i.e. the smallest passable area of the medical device 600, being an area of a hole through which said medical device 600 can pass is smaller than the smallest passable area of the caput femur 5, being an area of a hole through which said caput femur 5 can pass.

Figure 29B:
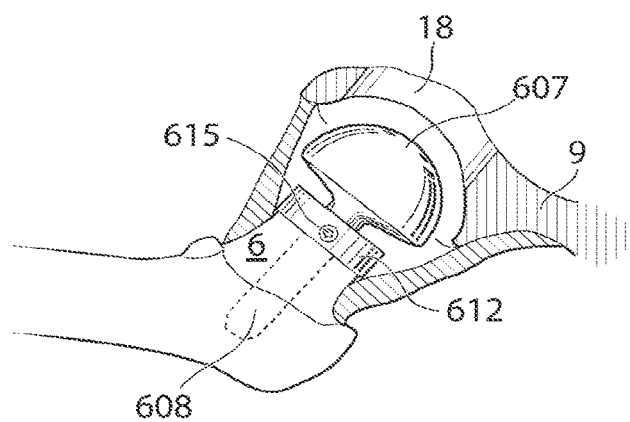

FIG. 29b shows the hip joint in section when the medical device 600 is positioned on the collum femur 6. The stabilizing member 612 is here fixated to the collum femur by means of adhesive 614 and a mechanical fixation element 615.

Figure 29C:
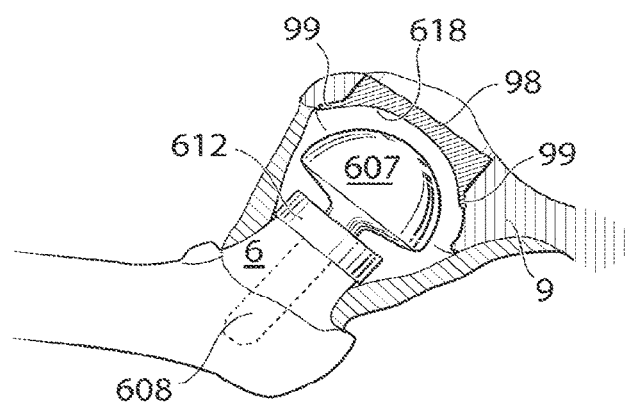

FIG. 29c shows the hip joint in section when the medical device 600 is positioned on the collum femur 6. The stabilizing member 612 is here fixated to the collum femur by means of adhesive 614. An prosthetic part 98 comprising an artificial acetabulum surface 618 has been positioned in the hole 18 in the pelvic bone 9. The artificial acetabulum surface 618 is adapted to be in direct of indirect connection with the artificial caput femur surface 607. In embodiments where the artificial acetabulum surface 618 is adapted to be in indirect connection with the artificial caput femur surface 607 a lubricating fluid or a lubricating material (not shown) can be placed between said artificial acetabulum surface 618 and said artificial caput femur surface 607. The prosthetic part is adapted to carry the load placed on the artificial acetabulum surface 618 from weight of the human patient through the contact with the artificial caput femur surface 607 by means of the supporting members 99 in connection with the pelvic bone. The prosthetic part 98 can further be fixated to the pelvic bone 9 by means of bone cement, adhesive, screws, form fitting, welding, sprints, band or some other mechanical connecting member. According to this embodiment the supporting members 99 are positioned on the acetabulum side of the pelvic bone 9, however it is also conceivable that the supporting members 99 are positioned on the abdominal side of the pelvic bone 9 or according to FIG. 35.

Figure 30A:
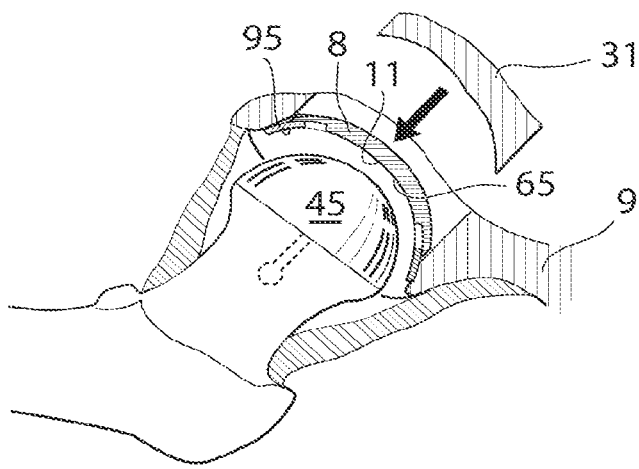

FIG. 30a shows the hip joint of a human patient in section, wherein a bone plug 31 is placed in the hole 18 in the pelvic bone 9 to close said hole 18. According to a first embodiment the medical device comprises supporting members 95 which carries the load placed on the acetabulum 8 from weight of the human patient through the contact with the caput femur 5. Said supporting members can be adapted to be displaceable 97 supporting members. The bone plug 31 can be attached to the artificial acetabulum surface 11 and/or the pelvic bone 9 by means of at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members.

The connection between the medical device and the pelvic bone 9 can be direct or indirect. In the embodiment where the contact between the medical device and the pelvic bone 9 is indirect, a material can be provided between said medical device and said pelvic bone. The material could comprise bone cement, an at least partly elastic material, glue, adhesive, antibiotic, biocompatible plastic material, biocompatible ceramics and/or biocompatible metal.

Figure 30B:
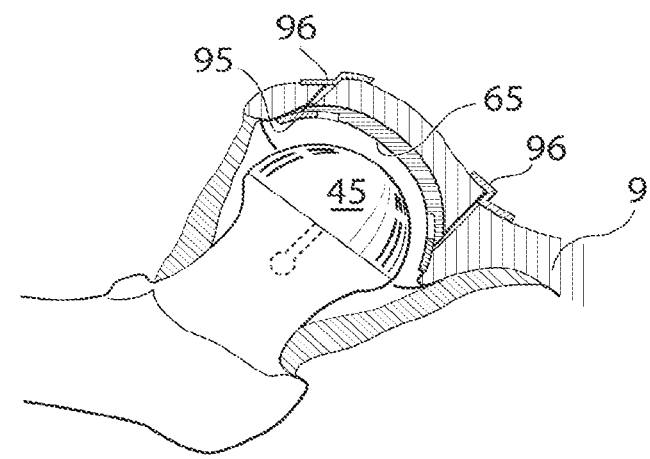

FIG. 30b shows the hip joint of a human patient in section wherein the bone plug 31 placed in the hole 18 in the pelvic bone 9 is further supported by supporting members 96 placed between the bone plug 31 and the pelvic bone 9 on the opposite side from acetabulum 8 using at lest one of: at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members.

Figure 31:
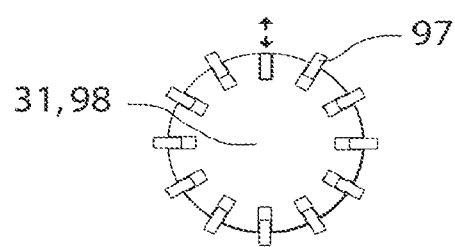
FIG. 31 shows a part for closing a hole in the pelvic bone having displaceable supporting members.

FIG. 31 shows a bone plug 31 or a prosthetic part 98 comprising several displaceable supporting members adapted to carry the load placed on the acetabulum 8 from weight of the human patient through the contact with the caput femur 5. The displaceable parts 97 are displaced into a corresponding part in or at the edge of the hole 18 in the pelvic bone 9.

Figure 32A:
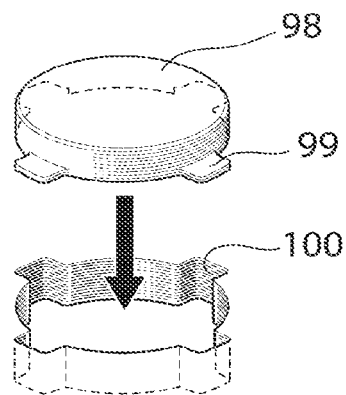
FIG. 32a shows a prosthetic part being used to close a hole in the pelvic bone.

FIG. 32a shows an embodiment wherein the closing of the hole 18 in the pelvic bone is performed by means of a prosthetic part 98. FIG. 56a shows the prosthetic part 98 being inserted into a hole 18 in the pelvic bone 9 from the opposite side from acetabulum 8. According to one embodiment the prosthetic part 98 comprises supporting members 99 adapted to correspond with sections 100 of the hole 18 in the pelvic bone 9. After the prosthetic part 98 has been inserted into said hole 18 in the pelvic bone 9 it is rotated so that the supporting members 99 comes in contact with the pelvic bone 9 and can carry the load placed on the acetabulum 8 from weight of the human patient through the contact with the caput femur 5. Said prosthetic part 98 could also be adapted to serve as artificial acetabulum surface 65 according to any of the above mentioned embodiments.

Figure 32B:
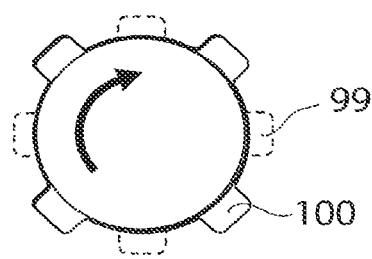
FIG. 32b shows how sections of a prosthetic part is used as support against the edges of the hole in the pelvic bone.

FIG. 32b shows the prosthetic part 98 when rotated to carry the load placed on the acetabulum 8 from weight of the human patient through the contact with the caput femur 5.

This supporting means could be constructed in many different ways and this should be seen as examples.

Figure 33:
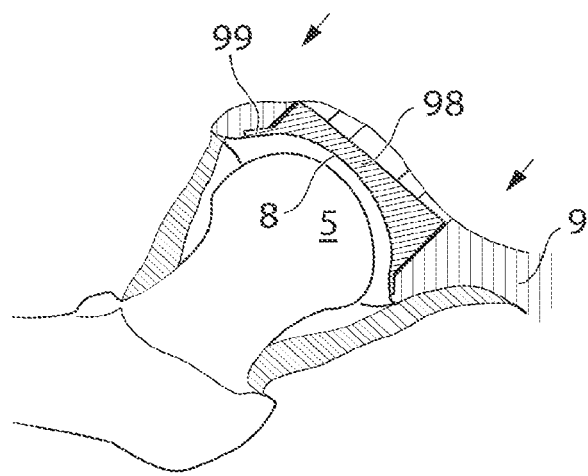
FIG. 33 shows the insertion of a prosthetic part in the hole in the pelvic bone.

FIG. 33 shows the hip joint of a human patient in section, wherein the prosthetic part 98 closes the hole 18 in the pelvic bone 9 and carries the load placed on the acctabulum 8 from weight of the human patient through the contact with the caput femur 5 by means of the supporting members 99. The prosthetic part 98 can further be fixated to the pelvic bone 9 by means of at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members.

Figure 34A:
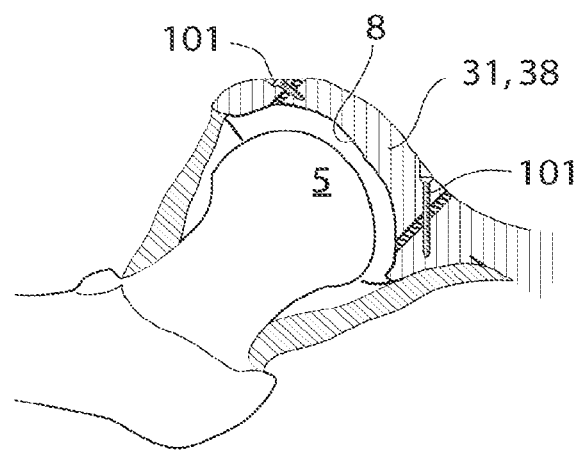
FIG. 34a shows how screws are being used to fixate a bone plug or a prosthetic part in the hole in the pelvic bone of a human patient.

FIG. 34a shows the hip joint of a human patient in section wherein bone plug 31 or prosthetic part 98 is attached to the pelvic bone 9 by means of screws 101 placed from the opposite side from acetabulum 8. The screws 101 are possible to place in different angles depending on reach or need for support. This construction may be performed in many different ways, for example using a plate mounted to the pelvic bone.

Figure 34B:
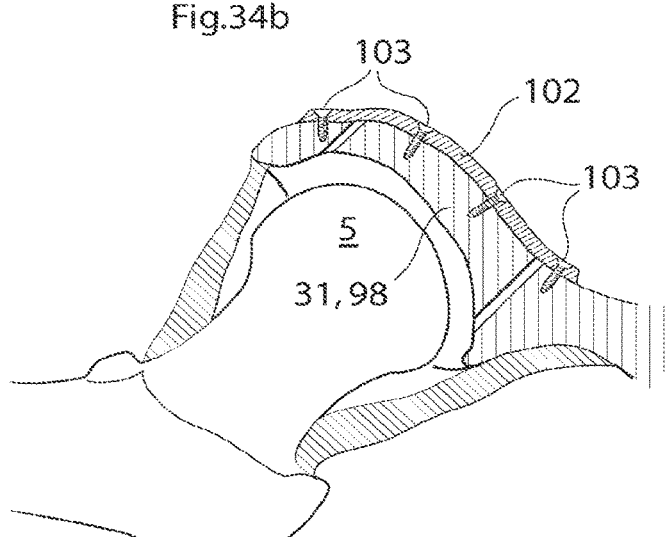
FIG. 34b shows how a supporting plate is being used to fixate a bone plug or a prosthetic part in the hole in the pelvic bone of a human patient.

FIG. 34b shows the hip joint of a human patient in section wherein bone plug 31 or prosthetic part 98 is attached to the pelvic bone 9 by means of a plate 102 at least partly covering said bone plug 31 or prosthetic part 98. According to a first embodiment the plate 102 is attached to the pelvic bone 9 by means of screws 103 placed from the opposite side from acetabulum 8. However it is also conceivable that said screws 103 can be replaced or assisted by bone cement, adhesive, form fitting, welding, sprints, band or some other mechanical connecting member.

Figure 34C:
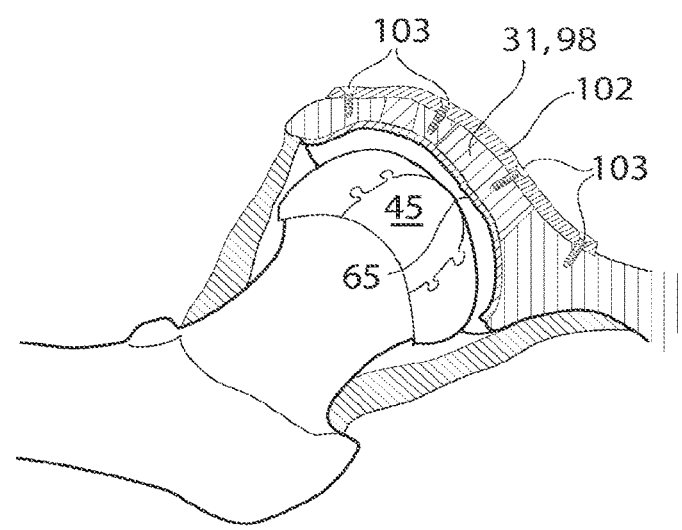
FIG. 34c shows two bone plugs or prosthetic parts being fixated using a supporting plate.

FIG. 34c shows the hip joint of a human patient in section wherein two bone plugs 31 or prosthetic parts 98 are attached to the pelvic bone 9 by means of a plate 102 at least partly covering said bone plugs 31 or prosthetic parts 98. According to a first embodiment the plate 102 is attached to the pelvic bone 9 by means of screws 103 placed from the opposite side from acetabulum 8. However it is also conceivable that said screws 103 can be replaced or assisted by bone cement, adhesive, form fitting, welding, sprints, band or some other mechanical connecting member.

FIG. 34c also shows the provided artificial acetabulum surface 65 and the provided caput femur surface. The members for fixating and covering the hole in the pelvic bone, together with the artificial acetabulum surface and the artificial caput femur surface constitute the medical device.

Figure 34D:
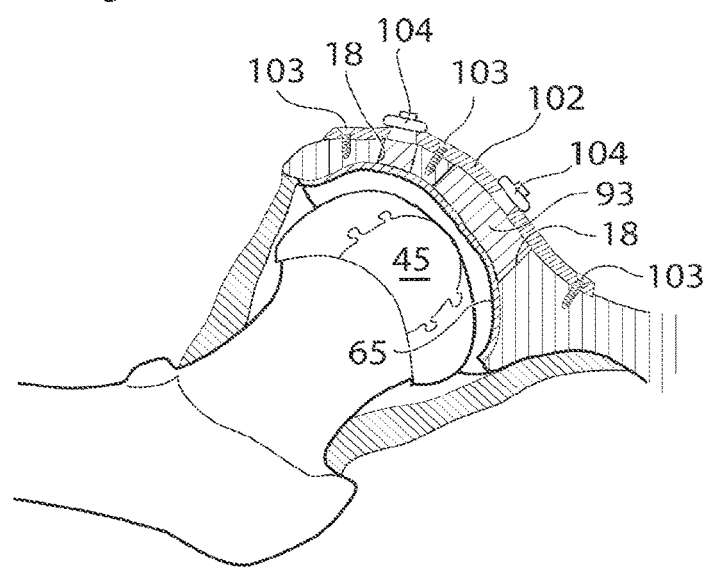
FIG. 34d shows a section of the hip joint after two holes in the pelvic bone have been filled with a fluid.

FIG. 34d shows the hip joint of a human patient in section wherein two holes 18 in the pelvic bone has been covered by means of a fluid injected into said holes 18, through sealing members 104, said fluid 93 being adapted to harden. Further more a plate 102 has been provided at least partly covering said holes 18. According to a first embodiment the plate 102 is attached to the pelvic bone 9 by means of screws 103 placed from the opposite side from acetabulum 8. However it is also conceivable that said screws 103 can be replaced or assisted by bone cement, adhesive, form fitting, welding, sprints, band or some other mechanical connecting member. FIG. 34d also shows the provided artificial acetabulum surface 65, and the provided artificial caput femur surface 45.

Figure 35:
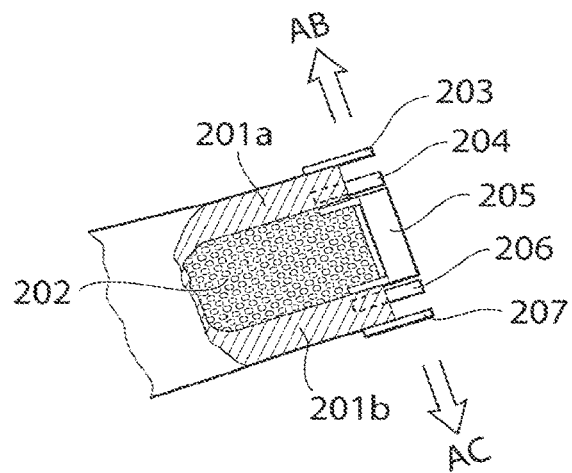
FIG. 35 shows, schematically, the pelvic bone in section.

FIG. 35 is a schematic figure of the pelvic bone in section, describing in further detail the supporting members shown in for example FIG. 35. The pelvic bone comprises an inner cortex 201a placed on the abdominal side of the pelvic bone AB, and an outer cortex 201b placed on the acetabulum side of the pelvic bone AC. The inner and outer cortex 201a,b comprises cortical bone, which is a more dense sclerotic bone. The pelvic bone further comprises cancellous bone 202, placed in the bone marrow between said inner cortex 201a and said outer cortex 201b. The supporting members of the medical device according to any of the embodiments above can be adapted to be in contact with the outside of the inner cortex 201a as supporting member 203, or be placed inside of the inner cortex 201a as supporting member 204, which enables the supporting member to carry loads in the direction of the abdomen AB as well as in the direction of the acetabulum AC. It is furthermore conceivable that the supporting member is placed in the middle of the inner cortex 201a and the outer cortex 201b, in the cancellous bone, as supporting member 205, in which case the supporting member could be in contact with the inner cortex 201a, on the inside thereof, and the outer cortex 201b, on the inside thereof, which enables the supporting member to carry loads in the direction of the abdomen AB as well as in the direction of the acetabulum AC. Further, the supporting members can be adapted to be in contact with the outside of the outer cortex 201b as supporting member 207, or be placed inside of the outer cortex 201b as supporting member 206, which enables the supporting member to carry loads in the direction of the abdomen AB as well as in the direction of the acetabulum AC.

Figure 36A:
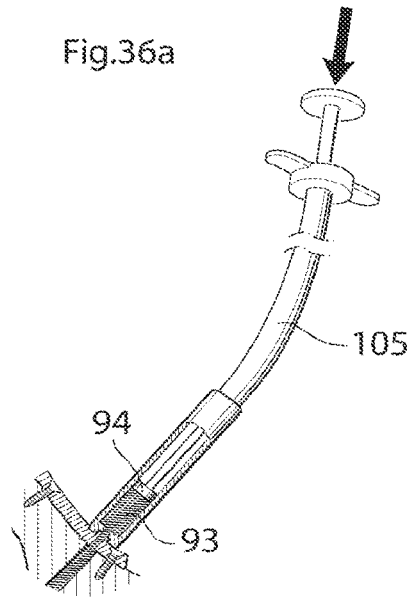
FIG. 36a shows an injecting member adapted to inject a fluid into an area of the hip joint.

FIG. 36a shows an injecting member 105 for injecting a fluid adapted to harden 93, preferably bone cement or adhesive to be used as support in the closing of the hole 18 in the pelvic bone 9. The injecting member 105 comprises a piston 94 that pushes said fluid 93 in to the area where it is wanted.

Figure 36B:
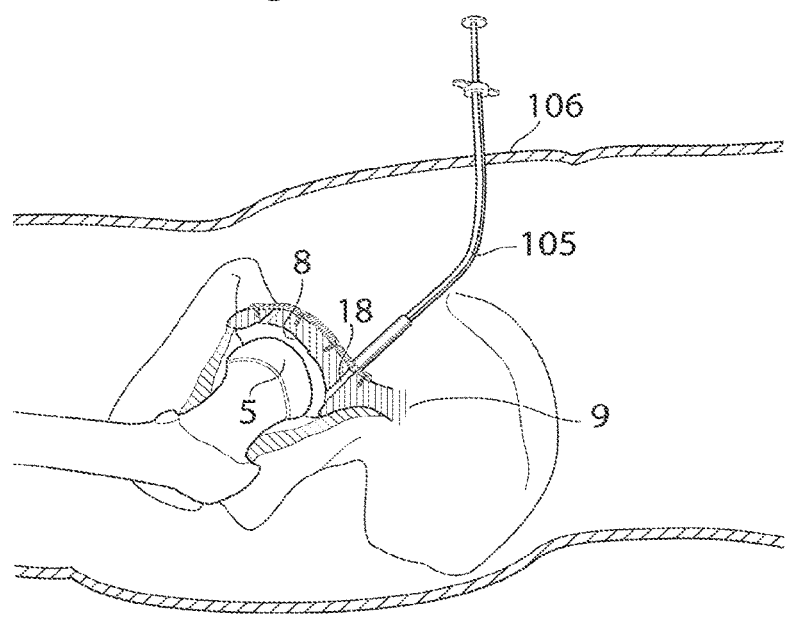
FIG. 36b shows an injecting member adapted to inject a fluid into an area of the hip joint when injecting a fluid.

FIG. 36b shows the injecting member 105 as it is inserted through the skin 106 of a human patient in the surgical or laparoscopic method, and is further placed in connection with the hip joint through the hole 18 in the pelvic bone 9. The injecting member 105 is adapted to inject a fluid 93 adapted to harden.

Figure 37:
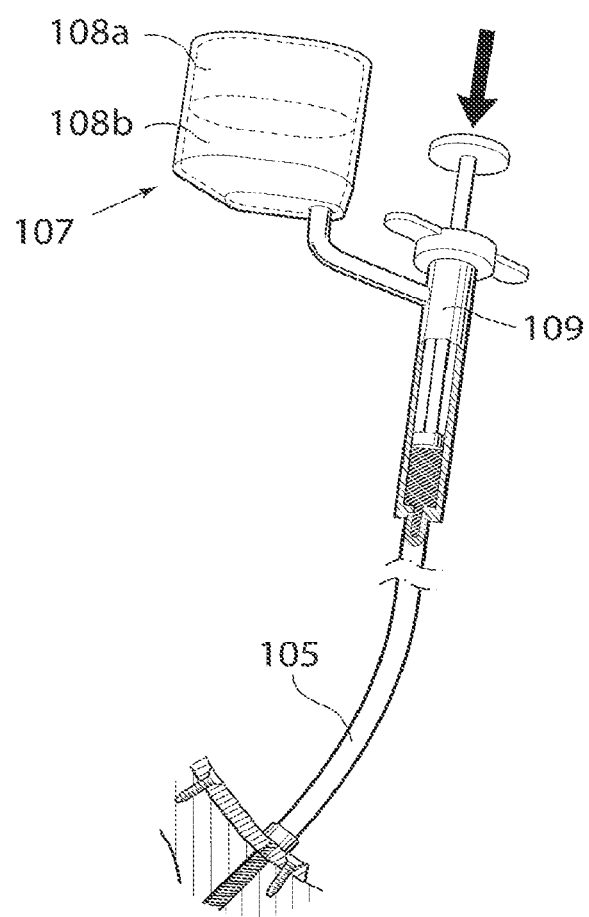
FIG. 37 shows an injecting member in further detail.

FIG. 37 shows the injecting member 105 according to any of the embodiments above, adapted to inject fluid 93 into a mould 81, a sealed area 87 or a connecting area between the pelvic bone 9 and a prosthetic part, the pelvic bone 9 and a bone plug 31 or the caput femur 5 and a prosthetic part. Said injecting member comprises a container 107 adapted to hold a fluid for injection. According to a first embodiment said container comprises two compartments 108a,b adapted to hold two different fluids, said fluids being adapted to harden when mixed. In the embodiment when the container 107 is adapted to hold two fluids, it is conceivable that the injecting member 105 further comprises a mixing member 109 wherein said two fluids are being mixed before injection. According to a second embodiment (not shown) said container 107 is adapted to keep said fluid sterile. According to a third embodiment (not shown) said container 107 is adapted to keep said fluid cold and according to a fourth embodiment (not shown) said container 107 is adapted to keep said fluid in a dark environment. Furthermore a combination of the above mentioned embodiments is conceivable.

After the step of closing the hole in the pelvic bone of the human patient is concluded the medical device has been provided and all instruments are retracted. The final step of a surgical or laparoscopic method comprises suturing or stapling the affected tissue and finally suturing or stapling the skin of the human patient.

Figure 38A:
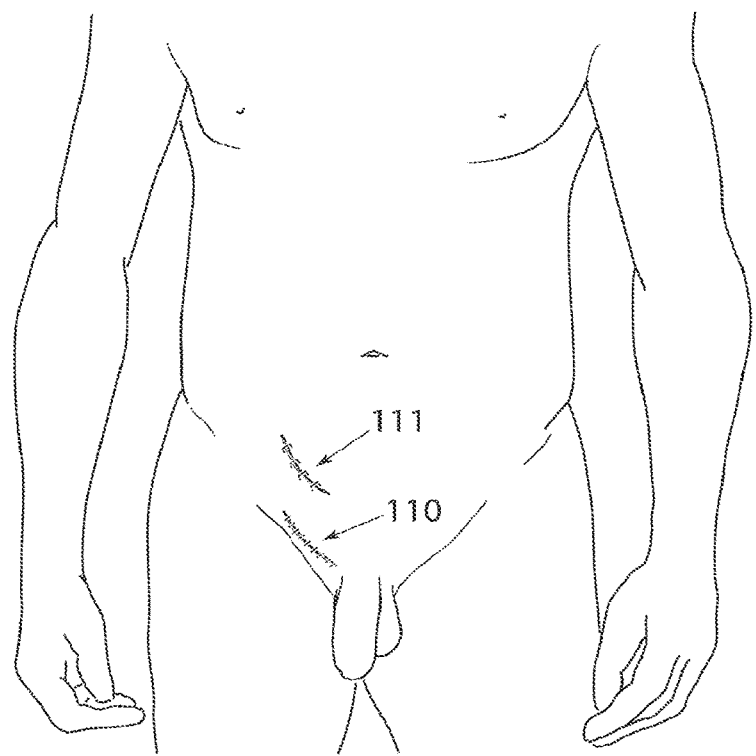
FIG. 38a shows the step of suturing or stapling in the surgical method.
Figure 38B:
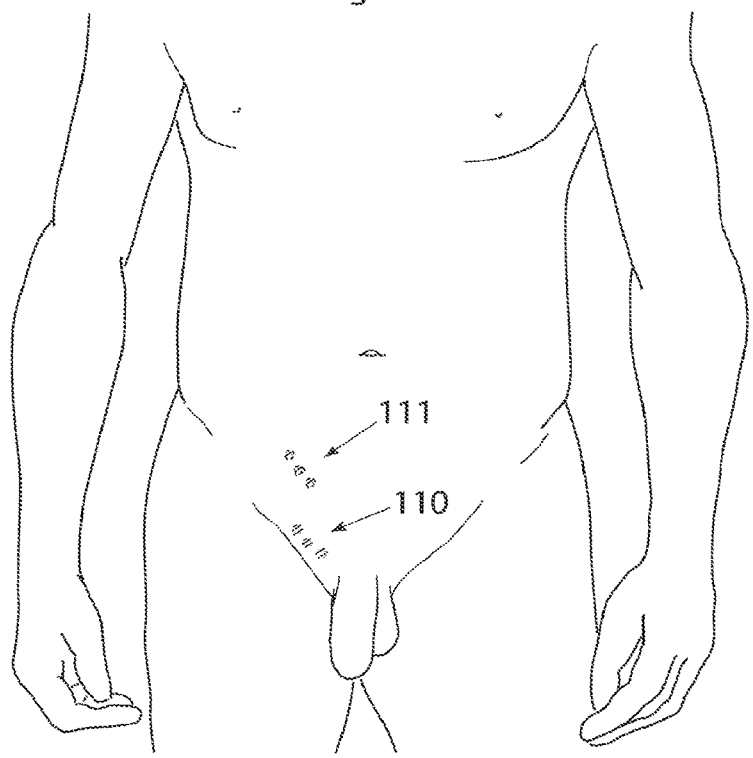
FIG. 38b shows the step of suturing or stapling in the laparoscopic method.

FIG. 38a shows the step of suturing 110 or stapling 111 the skin of the human patient in the surgical method, whereas FIG. 38b shows the step of suturing 110 or stapling 111 the skin of the human patient in the laparoscopic method. The laparoscopic method may not need any suturing.

Please note that any embodiment or part of embodiment as well as any method or part of method could be combined in any way. All examples herein should be seen as part of the general description and therefore possible to combine in any way in general terms.

The invention claimed is:

1. A method for treating hip joint osteoarthritis in a human patient by providing at least one medical device comprising an artificial hip joint surface, the hip joint comprising an acetabulum, being a part of a pelvic bone, and a caput femur being a part of a femoral bone, and having a partly spherical form having a largest diameter, wherein said medical device comprises:
a prosthetic part adapted to function as an articulating surface comprising a center axis generally coinciding with the acetabulum and the caput femur center axis when implanted,
the method comprising the steps of:
placing the prosthetic part in a through-going hole in the pelvic bone from an abdominal side opposite a concave portion of the acetabulum of the human patient,
radially displacing a plurality of displaceable protruding supporting members distributed circumferentially around the prosthetic part
such that the plurality of displaceable protruding supporting members are configured to transfer load from the prosthetic part via the displaceable connection to the pelvic bone when being displaced relative said prosthetic part in a direction more perpendicular than parallel to the prosthetic part's center axis and being implanted.

2. The method according to claim 1, wherein said medical device comprises at least two parts, and wherein said at least two parts are adapted to be connected to each other after insertion in the hip joint.

3. The method according to claim 1, wherein said medical device further comprises at least one of an artificial caput femur surface or an artificial acetabulum surface.

4. The method according to claim 3, when said medical device comprises the artificial caput femur surface and wherein said artificial caput femur surface is adapted to have a varying maximum diameter for insertion through a hole in the pelvic bone from the side opposite the concave portion of the acetabulum of the human patient, said hole having a diameter smaller than said largest diameter of the caput femur.

5. The method according to claim 3, when said medical device comprises the artificial caput femur surface and wherein said artificial caput femur surface is adapted to have a varying maximum diameter for insertion through a hole in the pelvic bone from the side opposite the concave portion of the acetabulum of the human patient, said hole having a diameter smaller than said largest diameter of said artificial caput femur surface, when said artificial caput femur surface is placed in a functional hip joint.

6. The method according to claim 3, when said medical device comprises the artificial acetabulum surface and wherein said artificial acetabulum surface is adapted to have a varying maximum diameter for insertion through a hole in the pelvic bone from the side opposite the concave portion of the acetabulum of said human patient, said hole having a diameter smaller than said largest diameter of said artificial acetabulum surface, when said artificial acetabulum surface is placed in a functional hip joint.

7. The method according to claim 3, when said medical device comprises the artificial acetabulum surface and wherein said hole has a diameter and wherein largest diameter of said artificial acetabulum surface is larger than said hole, thus said medical device being adapted to hinder said artificial acetabulum surface from passing through said hole, after being placed in a functional hip joint.

8. The method according to claim 3, when said medical device comprises the artificial caput femur surface and wherein said artificial caput femur surface comprises a replacement of the entire caput femur.

9. The method according to claim 1, wherein said at least one supporting member is adapted in a manner selected from the group comprising:
   in connection with the bone surrounding said hole, and wherein the bone directly or indirectly carries said load, adapted to be fixated through an inner cortex of the pelvic bone to carry said load, or
   adapted to be fixated to a surface of the pelvic bone which is opposite the concave portion of the acetabulum to carry said load.

10. A method for treating hip joint osteoarthritis in a human patient by providing a medical device comprising at least one artificial hip joint surface, the hip joint comprising an acetabulum, being a part of a pelvic bone, and a caput femur being a part of a femoral bone, and having a partly spherical form having a largest diameter, wherein said medical device comprises:
    a prosthetic part adapted to function as an articulating surface comprising a center axis generally coinciding with the acetabulum and the caput femur center axis when implanted, wherein said prosthetic part comprises the artificial acetabulum surface,
    the method comprising the steps of:
      placing the prosthetic part in a through-going hole in the pelvic bone from an abdominal side opposite a concave portion of the acetabulum of the human patient,
      radially displacing a plurality of displaceable supporting members distributed circumferentially around the prosthetic part such that said plurality of supporting members are displaceably connected to the prosthetic part, and configured to transfer load from the prosthetic part, via the displaceable connection, to the pelvic bone, when implanted, and wherein said at least one artificial hip joint surface is configured to function as an articulating surface and said displaceable protruding supporting member is configured to transfer load acting in the direction of the acetabulum and caput femur center axis, when the displaceable protruding supporting member is displaced in a direction more perpendicular than parallel to the prosthetic part's axis and is implanted.

11. The method according to claim 10, wherein said medical device comprises at least two parts, and wherein said at least two parts are adapted to be connected to each other after insertion in a hip joint.

12. The method according to claim 10, wherein said medical device further comprises an artificial caput femur surface.

13. The method according to claim 12, wherein said artificial caput femur surface comprises at least two caput femur surface parts, and wherein said at least two artificial caput femur surface parts are adapted to be connected to each other after insertion in a hip joint of a human patient to form an artificial caput femur surface.

14. The method according to claim 12, wherein said artificial caput femur surface is adapted to have a varying maximum diameter for insertion through a hole in the pelvic bone from the side opposite the concave portion of the acetabulum of the human patient, said hole having a diameter smaller than said largest diameter of the caput femur.

15. The method according to claim 12, wherein said artificial caput femur surface is adapted to have a varying maximum diameter for insertion through a hole in the pelvic bone from the side opposite the concave portion of the acetabulum of the human patient, said hole having a diameter smaller than said largest diameter of said artificial caput femur surface, when said artificial caput femur surface is placed in a functional hip joint.

16. The method according to claim 10, wherein said artificial acetabulum surface is adapted to have a varying maximum diameter for insertion through a hole in the pelvic bone from the side opposite the concave portion of the acetabulum of said human patient, said hole having a diameter smaller than said largest diameter of said artificial acetabulum surface, when said artificial acetabulum surface is placed in a functional hip joint.

17. The method according to claim 10, wherein said largest diameter of said artificial acetabulum surface is configured to be larger than a diameter of said through-going hole, thus said medical device being adapted to hinder said artificial acetabulum surface from passing through said hole, after being placed in a functional hip joint.

18. The method according to claim 10, wherein said artificial acetabulum surface comprises at least two acetabulum surface parts, and wherein said at least two artificial acetabulum surface parts are adapted to be connected to each other after insertion in the hip joint of a human patient to form said artificial acetabulum surface.

19. The method according to claim 10, wherein said at least one supporting member is adapted in a manner selected from the group comprising:
    in connection with the bone surrounding said hole, and wherein the bone directly or indirectly carries said load, fixated through an inner cortex of the pelvic bone to carry said load, or
    fixated to a surface of the pelvic bone which is substantially opposite the concave portion of the acetabulum to carry said load.

20. A method for treating hip joint osteoarthritis in a human patient by providing a medical device comprising at least one artificial hip joint surface, the hip joint comprising an acetabulum, being a part of a pelvic bone, and a caput femur being a part of a femoral bone, and having a partly spherical form having a largest diameter, wherein said medical device comprises:

a prosthetic part adapted to function as an articulating surface comprising a center axis generally coinciding with the acetabulum and the caput femur center axis when implanted, wherein said prosthetic part comprises the artificial acetabulum surface, the method comprising the steps of:

placing the prosthetic part in a through-going hole in the pelvic bone from an abdominal side opposite a concave portion of the acetabulum of the human patient, circumferentially displacing a plurality of displaceable supporting members distributed circumferentially around the prosthetic part such that said plurality of supporting members are rotated relative the pelvic bone, and configured to transfer load from the prosthetic part, via the displaceable connection, to the pelvic bone, when implanted, and wherein said at least one artificial hip joint surface is configured to function as an articulating surface and said displaceable protruding supporting member is configured to transfer load acting in the direction of the acetabulum and caput femur center axis, when the displaceable protruding supporting member is displaced.

\* \* \* \* \*